US011090223B2

(12) United States Patent
Freeman et al.

(10) Patent No.: US 11,090,223 B2
(45) Date of Patent: Aug. 17, 2021

(54) INTEGRATED RESUSCITATION

(75) Inventors: Gary A. Freeman, Newton Center, MA (US); Mark Totman, Winchester, MA (US); David Barash, Concord, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 1438 days.

(21) Appl. No.: 11/391,708

(22) Filed: Mar. 27, 2006

(65) Prior Publication Data

US 2006/0270952 A1 Nov. 30, 2006

Related U.S. Application Data

(60) Provisional application No. 60/665,157, filed on Mar. 25, 2005.

(51) Int. Cl.
*A61H 31/00* (2006.01)
*A61N 1/39* (2006.01)
*A61B 5/11* (2006.01)

(52) U.S. Cl.
CPC .......... *A61H 31/005* (2013.01); *A61H 31/007* (2013.01); *A61N 1/39044* (2017.08);
(Continued)

(58) Field of Classification Search
CPC .... A61H 31/005; A61H 31/00; A61H 31/007; A61H 2201/002; A61H 2201/5007; A61H 2201/0543; A61H 2201/5048; A61H 2201/5058; A61H 2201/5071; A61H 2201/5084; A61H 2201/5097; A61H 2230/10; A61H 2230/207; A61H 2230/40; A61N 1/39044; A61N 1/3925; A61B 5/11
(Continued)

(56) References Cited

U.S. PATENT DOCUMENTS 5,239,988 A 8/1993 Swanson et al.
5,330,526 A 7/1994 Fincke et al.
(Continued)

FOREIGN PATENT DOCUMENTS

JP H05-14985 2/1993
WO 9115267 10/1991
(Continued)

OTHER PUBLICATIONS

Circulation. 2005;112:IV-19-IV-34.
FSR Integration Guide & Evaluation Parts Catalog with Suggested Electrical Interfaces from Interlink Electronics.

*Primary Examiner* — Timothy A Musselman
(74) *Attorney, Agent, or Firm* — ZOLL Medical Corporation

(57) ABSTRACT

A resuscitation device for assisting a rescuer in resuscitating a patient. A handheld computing/communication device may be configured for performing a non-resuscitation function during time periods when resuscitation is not required, the handheld device may be further configured to provide CPR prompts during time periods when used by a rescuer to assist in resuscitation, and a sensor may be provided to measure a parameter (e.g., chest acceleration) relevant to resuscitation. A CPR-assistance element may be configured to be applied to the patient and to communicate with the handheld computing/communication device.

34 Claims, 21 Drawing Sheets

(52) U.S. Cl.
CPC ........... *A61B 5/11* (2013.01); *A61H 2031/002* (2013.01); *A61H 2201/5007* (2013.01); *A61H 2201/5043* (2013.01); *A61H 2201/5048* (2013.01); *A61H 2201/5058* (2013.01); *A61H 2201/5071* (2013.01); *A61H 2201/5084* (2013.01); *A61H 2201/5097* (2013.01); *A61H 2230/04* (2013.01); *A61H 2230/10* (2013.01); *A61H 2230/207* (2013.01); *A61H 2230/40* (2013.01); *A61N 1/3925* (2013.01)

(58) Field of Classification Search
USPC .............. 434/262, 275, 265; 607/5; 601/41; 600/301
See application file for complete search history.

(56) References Cited

U.S. PATENT DOCUMENTS

| | | | |
|---|---|---|---|
| 5,496,257 A * | 3/1996 | Kelly | 601/41 |
| 5,544,661 A * | 8/1996 | Davis et al. | 600/513 |
| 5,617,853 A * | 4/1997 | Morgan | 600/386 |
| 5,944,018 A | 8/1999 | Allgood et al. | |
| 6,306,107 B1 * | 10/2001 | Myklebust | A61B 5/1036 |
| | | | 128/897 |
| 6,351,671 B1 | 2/2002 | Myklebust et al. | |
| 6,356,785 B1 | 3/2002 | Snyder et al. | |
| 6,485,416 B1 * | 11/2002 | Platt et al. | 600/300 |
| 6,546,232 B1 | 4/2003 | Sack et al. | |
| 6,599,258 B1 * | 7/2003 | Bystrom et al. | 601/41 |
| 6,807,442 B1 * | 10/2004 | Myklebust et al. | 600/509 |
| 6,861,946 B2 * | 3/2005 | Verplaetse | G06F 1/1626 |
| | | | 340/315 |
| 6,969,259 B2 * | 11/2005 | Pastrick et al. | 434/265 |
| 7,074,199 B2 * | 7/2006 | Halperin et al. | 601/41 |
| 7,122,014 B2 * | 10/2006 | Palazzolo | A61B 5/04012 |
| | | | 601/41 |
| 7,131,953 B2 * | 11/2006 | Sherman et al. | 601/41 |
| 7,220,235 B2 * | 5/2007 | Geheb et al. | 601/41 |
| 7,289,029 B2 * | 10/2007 | Medema et al. | 340/573.1 |
| 7,310,553 B2 * | 12/2007 | Freeman | 607/5 |
| 7,530,840 B2 * | 5/2009 | Lund et al. | 439/501 |
| 7,565,194 B2 * | 7/2009 | Tan et al. | 607/2 |
| 7,567,180 B2 * | 7/2009 | Blevins et al. | 340/573.1 |
| 7,645,247 B2 * | 1/2010 | Paradis | 601/41 |
| 7,650,181 B2 * | 1/2010 | Freeman et al. | 600/510 |
| 7,706,878 B2 * | 4/2010 | Freeman | 607/6 |
| 7,774,054 B2 * | 8/2010 | Myklebust | 600/547 |
| 7,774,060 B2 * | 8/2010 | Westenskow et al. | 607/5 |
| 9,125,793 B2 * | 9/2015 | Palazzolo | A61H 31/005 |
| 2001/0047140 A1 | 11/2001 | Freeman | |
| 2002/0055694 A1 * | 5/2002 | Halperin | A61B 5/11 |
| | | | 601/41 |
| 2002/0143576 A1 | 10/2002 | Nolvak et al. | |
| 2003/0025602 A1 * | 2/2003 | Medema et al. | 340/568.1 |
| 2003/0036044 A1 * | 2/2003 | Pastrick | G09B 23/288 |
| | | | 434/265 |
| 2003/0055458 A1 * | 3/2003 | Hamilton | A61N 1/39 |
| | | | 607/5 |
| 2003/0069510 A1 | 4/2003 | Semler | |
| 2003/0109904 A1 * | 6/2003 | Silver et al. | 607/59 |
| 2003/0144699 A1 | 7/2003 | Freeman | |
| 2003/0192547 A1 | 10/2003 | Lurie et al. | |
| 2004/0133244 A1 * | 7/2004 | Vaisnys | A61N 1/39 |
| | | | 607/5 |
| 2004/0155772 A1 | 8/2004 | Medema et al. | |
| 2004/0172069 A1 * | 9/2004 | Hakala | 607/5 |
| 2004/0210171 A1 * | 10/2004 | Palazzolo et al. | 601/41 |
| 2004/0214148 A1 | 10/2004 | Salvino et al. | |
| 2004/0267325 A1 * | 12/2004 | Geheb | A61B 5/11 |
| | | | 607/5 |
| 2005/0013957 A1 * | 1/2005 | Leschinsky | B32B 7/06 |
| | | | 428/40.1 |
| 2005/0037730 A1 | 2/2005 | Montague | |
| 2005/0131465 A1 * | 6/2005 | Freeman et al. | 607/5 |
| 2005/0212749 A1 * | 9/2005 | Marvit | G06F 1/1613 |
| | | | 345/156 |
| 2005/0251213 A1 * | 11/2005 | Freeman | 607/5 |
| 2006/0094949 A1 * | 5/2006 | Coonce | A61B 5/0002 |
| | | | 600/407 |
| 2006/0129191 A1 * | 6/2006 | Sullivan | A61N 1/39 |
| | | | 607/5 |
| 2006/0178041 A1 * | 8/2006 | Lund et al. | 439/501 |
| 2006/0270952 A1 * | 11/2006 | Freeman et al. | 601/41 |

FOREIGN PATENT DOCUMENTS

| | | |
|---|---|---|
| WO | 99/004687 | 2/1999 |
| WO | 99/24114 | 5/1999 |
| WO | WO01/13791 | 3/2001 |
| WO | 01/56652 | 8/2001 |
| WO | WO02/30279 | 4/2002 |

* cited by examiner

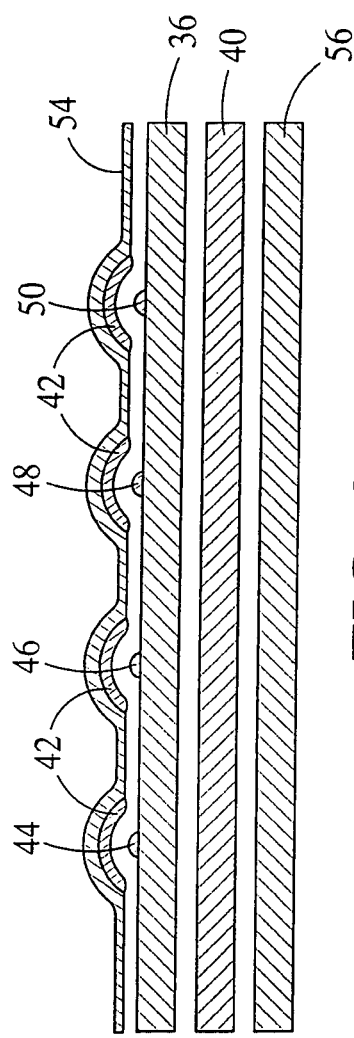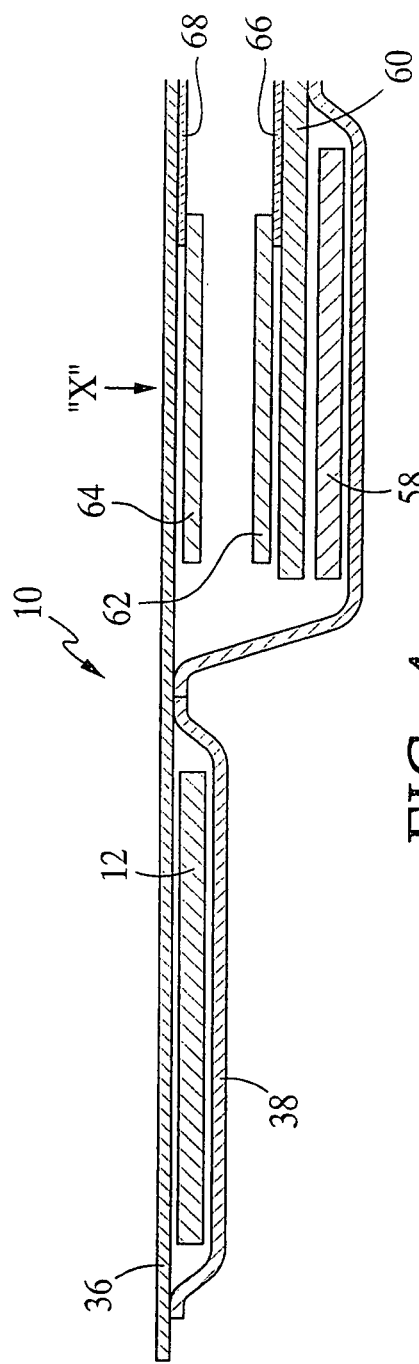

INTEGRATED RESUSCITATION

CROSS-REFERENCE TO RELATED APPLICATION

This application claims priority from U.S. Provisional Application Ser. No. 60/665,157, filed Mar. 25, 2005.

TECHNICAL FIELD

This invention relates to resuscitation systems incorporating defibrillation therapy and resuscitation prompts.

BACKGROUND

Resuscitation can generally include clearing a patient's airway, assisting the patient's breathing, chest compressions, and defibrillation.

The American Heart Association's Basic Life Support for Health Care Providers textbook provides a flow chart at page 4-14 of Chapter 4 that lists the steps of airway clearing, breathing, and circulation (known as A, B, and C), for situations in which there is no defibrillator readily accessible to the rescuer. Defibrillation (sometimes known as step D) can be performed with the use of an automatic external defibrillator (AED). Most automatic external defibrillators are actually semi-automatic external defibrillators (SAED), which require a clinician to press a start button, after which the defibrillator analyzes the patient's condition and provides a shock to the patient if the electrical rhythm is shockable and waits for user intervention before any subsequent shock. Fully automatic external defibrillators, on the other hand, do not wait for user intervention before applying subsequent shocks. As used below, automatic external defibrillators (AED) include semi-automatic external defibrillators (SAED).

Both types of defibrillators typically provide an oral stand clear warning before the application of each shock, and then the clinician is expected to stand clear of the patient and may be required to press a button indicating that the clinician is standing clear of the patient. The controls for automatic external defibrillators are typically located on a resuscitation control box.

AEDs are used typically by trained providers such as physicians, nurses, fire department personnel, and police officers. There might be one or two people at a given facility that has an AED who have been designated for defibrillation resuscitation before an ambulance service arrives. The availability of on-site AEDs along with rescuers trained to operate them is important because if the patient experiences a delay of more than 4 minutes before receiving a defibrillation shock the patient's chance of survival can drop dramatically. Many large cities and rural areas have low survival rates for defibrillation because the ambulance response time is slow, although many suburbs have higher survival rates because of the faster ambulance response time due to lack of traffic and availability of hospitals and advanced life support.

Trained lay providers are a new group of AED operators, but they rarely have opportunities to defibrillate. For example, spouses of heart attack victims may become lay providers, but these lay providers can be easily intimidated by an AED during a medical emergency. Consequently, such lay providers can be reluctant to purchase AEDs, or might tend to wait for an ambulance to arrive rather than use an available AED, out of concern that the lay provider might do something wrong.

There are many different kinds of heart rhythms, some of which are considered shockable and some of them are not. For example, a normal rhythm is considered non-shockable, and there are also many abnormal non-shockable rhythms. There are also some abnormal non-viable non-shockable, which means that the patient cannot remain alive with the rhythm, but yet applying shocks will not help convert the rhythm.

As an example of a non-shockable rhythm, if a patient experiences asystole, the heart will not be beating and application of shocks will be ineffective. Pacing is recommended for asystole, and there are other things that an advanced life support team can do to assist such patient, such as the use of drugs. The job of the first responder is simply to keep the patient alive, through the use of CPR and possibly defibrillation, until an advanced life support team arrives. Bradycardias, during which the heart beats too slowly, are non-shockable and also possibly non-viable. If the patient is unconscious during bradycardia, it can be helpful to perform chest compressions until pacing becomes available. Electro-mechanical dissociation (EMD), in which there is electrical activity in the heart but it is not making the heart muscle contract, is non-shockable and non-viable, and would require CPR as a first response. Idio-ventricular rhythms, in which the normal electrical activity occurs in the ventricles but not the atria, can also be non-shockable and non-viable (usually, abnormal electrical patterns begin in the atria). Idio-ventricular rhythms typically result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles.

The primary examples of shockable rhythms, for which a first responder should perform defibrillation, include ventricular fibrillation, ventricular tachycardia, and ventricular flutter.

After using a defibrillator to apply one or more shocks to a patient who has a shockable electrical rhythm, the patient may nevertheless remain unconscious, in a shockable or non-shockable rhythm. The rescuer may then resort to chest compressions (alternatively, chest compressions may be applied prior to the initial delivery of a shock). As long as the patient remains unconscious, the rescuer can alternate between use of the defibrillator (for analyzing the electrical rhythm and possibly applying a shock) and performing cardio-pulmonary resuscitation (CPR).

CPR generally involves a repeating pattern of five or fifteen chest compressions followed by a pause. CPR is generally ineffective against abnormal rhythms, but it does keep some level of blood flow going to the patient's vital organs until an advanced life support team arrives. It is difficult to perform CPR over an extended period of time. Certain studies have shown that over a course of minutes, rescuers tend to perform chest compressions with less-than-sufficient strength to cause an adequate supply of blood to flow to the brain. CPR prompting devices can assist a rescuer by prompting each chest compression and breath.

PCT Patent Publication No. WO 99/24114, filed by Heartstream, Inc., discloses an external defibrillator having PCR and ACLS (advanced cardiac life support) prompts.

U.S. Patent Application 2005/0037730 discloses a wireless phone with a motion sensor used to detect an emergency situation such as an automobile crash.

SUMMARY

In a first aspect, the invention features a resuscitation device for assisting a rescuer in resuscitating a patient, comprising a handheld computing/communication device configured for performing a non-resuscitation function during time periods when resuscitation is not required; the handheld device being further configured to provide CPR prompts during time periods when used by a rescuer to assist in resuscitation, and the handheld device including a sensor configured to measure a parameter relevant to the performance of cardiac resuscitation.

Preferred implementations of this aspect of the invention may incorporate one or more of the following. The device may comprise circuitry for functioning as a cell phone. The device may comprise circuitry for functioning as a personal digital assistant (PDA). The device may further comprise a dedicated button for activating a CPR prompting function. The sensor may comprise a motion sensor and may be configured to sense chest motion from which chest compression is estimated by the device. The cell phone may be configured so that it may be placed between the rescuers hands and the patient's chest, with the force delivered for chest compression being delivered through the cell phone. The device may further comprise circuit elements for providing spatial location. The circuit element for providing spatial location may comprise GPS circuitry. The sensor may comprise a sensor for making one or more of the following measurements: ECG measurements, circulation measurements, ventilation measurements. A sensor for circulation measurements may comprise one or more of the following: pulse oximetry, ultrasound, impedance, heart or blood flow sounds. The sensor for ventilation measurements may comprise a sensor for making one or more of the following measurements: transthoracic impedance, airway pressure, or breathing sounds. The sensor may comprise elements for making one or more of the following measurements: ECG, oximetry, or transthoracic impedance measurements. The handheld computing/communication device may have the capability of communicating with an EMS service. The handheld device may have speaker phone capability to allow a lay rescuer to speak to the EMS service during a rescue. The device may be configured to communicate with a therapy delivery device. The therapy delivery device may comprise a defibrillator. The handheld computing/communication device comprises a structural element surrounding some portion of it to permit force to be applied through the device to the chest.

In a second aspect, the invention features a resuscitation device for assisting a rescuer in resuscitating a patient, comprising a CPR-assistance element configured to be applied to the patient's chest during resuscitation, wherein the CPR-assistance element is configured to communicate with a handheld computing/communication device configured for performing a non-resuscitation function during time periods when resuscitation is not required.

Preferred implementations of this aspect of the invention may incorporate one or more of the following. The CPR-assistance element may communicate data relating to the patient to the handheld computing/communication device, which may be further configured to provide CPR prompts based at least in part on the data received from the CPR-assistance element. The CPR-assistance element may further comprise a motion sensor and may be configured to be placed on the patient's chest to sense chest motion from which chest compression may be estimated. The CPR-assistance element may further comprise one or more sensors for making one or more of the following measurements: ECG measurements, circulation measurements, ventilation measurements. The CPR-assistance element may comprise circuitry for communicating wirelessly with the handheld computing/communication device. The CPR-assistance element may be configured to automatically activate the handheld computing/communication device. The CPR-assistance element may be a thin, card-like device. The CPR-assistance element may be configured to be activated by peeling away a release layer. Adhesive may be exposed by peeling away the release layer from the CPR-assistance element, and the exposed adhesive may be configured to be used to adhere the element to the patient's chest. Electrodes may be exposed in peeling away the release layer, and the electrodes and circuitry in the CPR-assistance element may be configured to be used to detect ECG or make other measurements of the patient. The CPR-assistance element may be configured to be positioned on the patient's chest so that chest compression forces are applied to it by a rescuer. The handheld computing/communication device to which the CPR-assistance element communicates may be a cell phone. The CPR-assistance element may be configured to be wearable by the patient. The CPR-assistance element may be adhered by adhesive to the sternum during CPR, and chest compression forces may be applied to it.

In a third aspect, the invention features a resuscitation device for assisting a rescuer in resuscitating a patient or for training a rescuer to resuscitate a patient, comprising a handheld device configured to be placed on the patient's chest during resuscitation so that the user presses down on the device to convey compressive force to the patient's chest; an accelerometer supported within the device for measuring acceleration of the patient's chest; processing circuitry within the device for estimating chest displacement from measured acceleration and for delivering spoken prompts to the user to assist the user in delivering chest compressions, a speaker for conveying the prompts to the user.

Preferred implementations of this aspect of the invention may incorporate one or more of the following. The prompts may inform the user either that he is delivering good compressions or that he should press harder. The device may further provides a repeating tone to provide the user with timing for delivery of compressions. The device further provides one or more visual indicators to provide the user with feedback as to whether the proper compression depth was achieved in delivering a compression. The device may further comprise an ECG electrode for measuring the patient's ECG, and the processing circuitry may be configured to determine whether a defibrillator should be used to treat the patient. The device may be configured to communicate with an external device (e.g., with a cell phone or other handheld computing/communication device).

Some implementations of the invention may permit wider distribution and availability of a unit capable of resuscitation prompting. Wider distribution of resuscitation units may mean more successful rescues, as a patient can be stabilized and prepared for defibrillation using the widely available unit.

Other features and advantages of the invention will be found in the detailed description, drawings, and claims.

DESCRIPTION OF DRAWINGS

FIG. 3 is a cross-sectional drawing of the defibrillation electrode pad of FIG. 1 taken along line 3-3.

FIG. 4 is a cross-sectional drawing of the defibrillation pad of FIG. 1 taken along line 4-4.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims. Not all of the implementations shown are implementations of the claims.

FIGS. 1 through 9B show implementations disclosed in commonly owned applications, Ser. No. 09/794,320, filed on Feb. 27, 2001, and Ser. No. 09/498,306, filed on Feb. 4, 2000. They provide useful background and context for the discussion of implementations shown in FIGS. 10 through 16.

Figure 1:
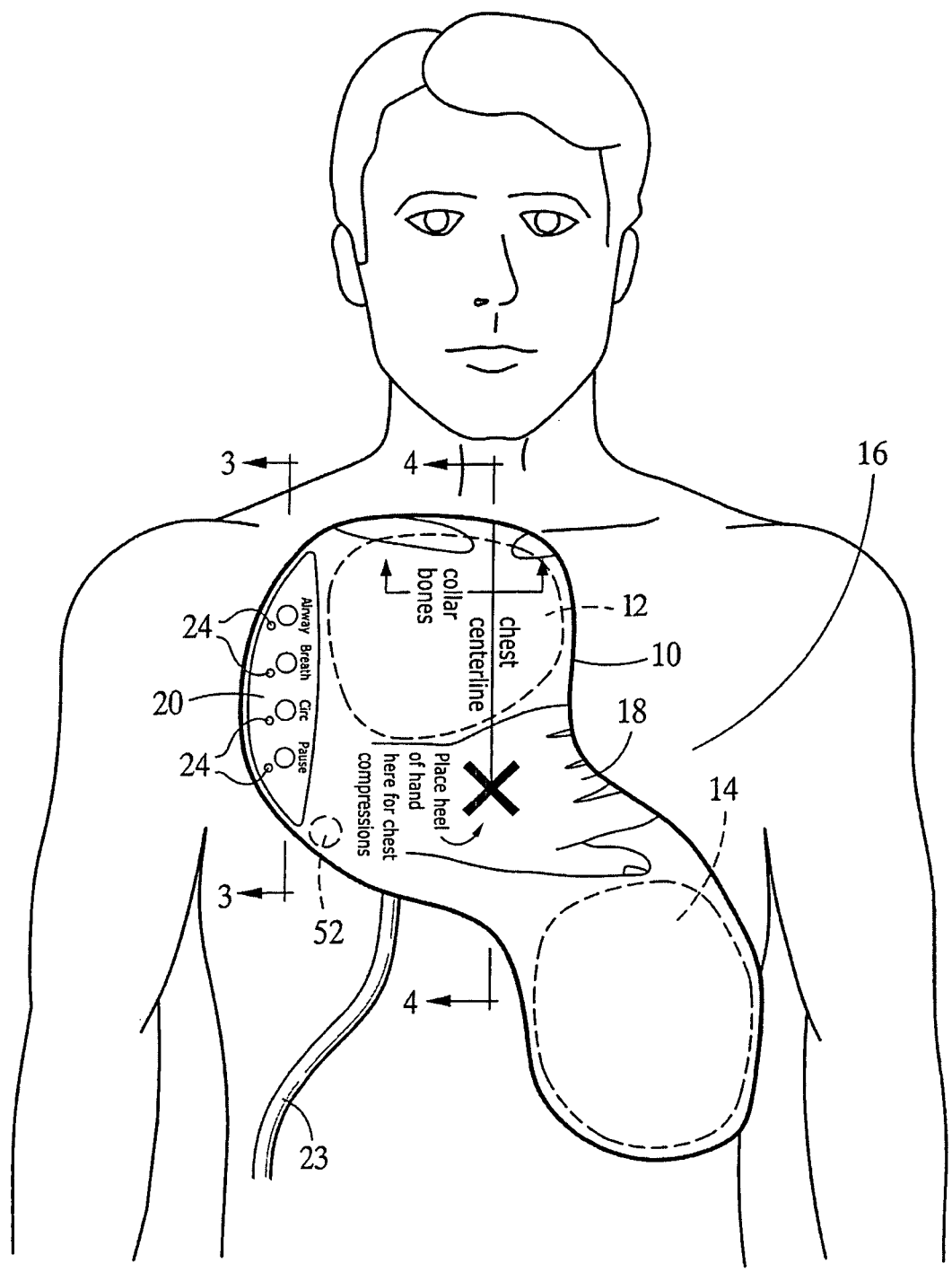
FIG. 1 is a drawing of a defibrillation electrode pad positioned over the chest of a patient.

With reference to FIG. 1, a defibrillation electrode pad 10, which includes high-voltage apex defibrillation electrode 12 and high-voltage sternum defibrillation electrode 14, is placed on the patient's chest 16 and includes a region 18 on which a user may press to perform CPR. Legends on pad 10 indicate proper placement of the pad with respect to the patient's collarbones and the chest centerline and the proper placement of the heel of the rescuer's hand.

A low-profile button panel 20 is provided on the electrode assembly. Button panel 20 has buttons 22, including buttons A (Airway Help), B (Breathing Help), C (Circulation Help) and PAUSE, and may also include adjacent light emitting diodes (LEDs) 24 that indicate which button has been most recently pressed. Button panel 20 is connected by a cable 23 to a remote resuscitation control box 26, shown in FIG. 2. Button panel 20 provides rigid support underneath buttons A, B, C, and PAUSE against which the switches can be pushed in order to ensure good switch closure while the electrode rests on a patient. Button panel 20 includes components that make electrical contact with silver/silver-chloride electrical circuit components screen-printed on a polyester base of defibrillation electrode pad 10, as is described in detail below.

A pulse detection system based on shining light through the patient's vascular bed, e.g., a pulse oximetry system 52, is incorporated into defibrillation electrode pad 10. Pulse oximetry system 52 includes a red light-emitting diode, a near-infrared light-emitting diode, and a photodetector diode (see FIG. 5) incorporated into defibrillation electrode pad 10 in a manner so as to contact the surface of the patient's chest 16. The red and near-infrared light-emitting diodes emit light at two different wavelengths, which is diffusely scattered through the patient's tissue and detected by the photodetector diode. The information obtained from the photodetector diode can be used to determine whether the patient's blood is oxygenated, according to known noninvasive optical monitoring techniques.

In another implementation, the pulse detection system is a phonocardiogram system for listening to the sound of the victim's heart, rather than a pulse oximetry system. The phonocardiogram system includes a microphone and an amplifier incorporated within the electrode pad. Because a heart sound can be confused with microphone noise, the signal processing that must be performed by the microprocessor inside the control box will be more difficult in connection with a phonocardiogram system than in connection with a pulse oximetry system. Nevertheless, there are programs available that can enable the microprocessor to determine whether an ECG signal is present as opposed to microphone noise.

Pulse oximetry is a well-developed, established technology, but it requires good contact between the light sources and the victim's skin so that light can shine down into the victim's vascular bed. Many victims have lots of chest hair, which can interfere with good contact. It may be desirable for different types of electrode pads to be available at a given location (one having a pulse oximetry system and one having a phonocardiogram system) so that a rescuer can select an appropriate electrode pad depending on the nature of the victim.

In another implementation, instead of providing a low-profile button panel, a button housing can be provided that is affixed to an edge of the defibrillation electrode. The housing may be in the form of a clamshell formed of single molded plastic element having a hinge at an edge of the clamshell around which the plastic bends. The two halves of the clamshell can be snapped together around the electrode assembly.

The resuscitation control box (FIG. 2) includes an internal charge storage capacitor and associated circuitry including a microprocessor, an further includes off/on dial 28, and a "READY" button 30 that the resucer presses immediately prior to application of a defibrillation shock in order to ensure that the rescuer is not in physical contact with the patient. The microprocessor may be a RISC processor such as a Hitachi SH-3, which can interface well with displays and keyboards, or more generally a processor capable of handling DSP-type (digital signal processing) operations.

The resuscitation control box has printed instructions 32 on its front face listing the basic steps A, B, and C for resuscitating a patient and giving basic instructions for positioning the defibrillation electrode pad on the patient. A speaker 32 orally prompts the user to perform various steps, as is described in detail below.

For example, the resuscitation control box instructs the user, by audible instructions and also through a display 34 on the resuscitation control box, to check the patient's airway and perform mouth-to-mouth resuscitation, and if the patient's airway is still blocked, to press the A (Airway Help) button on the button panel (FIG. 1), upon which the resuscitation control box gives detailed prompts for clearing the patient's airway. If the patient's airway is clear and the patient has a pulse but the patient does not breathe after initial mouth-to-mouth resuscitation, the resuscitation control box instructs the user press the B (Breathing Help) button, upon which the resuscitation control box gives detailed mouth-to-mouth resuscitation prompts. If, during the detailed mouth-to-mouth resuscitation procedure, the rescuer checks the patient's pulse and discovers that the patient has no pulse, the resuscitation control box instructs the user to press the C (Circulation Help) button.

During the circulation procedure, the resuscitation control box receives electrical signals from the defibrillation electrodes and determines whether defibrillation or CPR should be performed. If the resuscitation control box determines that defibrillation is desirable, the resuscitation control box instructs the user to press the "ready" button on the resuscitation control box and to stand clear of the patient. After a short pause, the resuscitation control box causes a defibrillation pulse to be applied between the electrodes. If at any point the resuscitation control box determines, based on the electrical signals received from the electrodes, that CPR is desirable, it will instruct the user to perform CPR.

Thus, the key controls for the system are on the electrodes attached to the patient rather than the resuscitation control box. This is important because it enables the rescuer to remain focused on the patient rather than the control box. The resuscitation control box gets its information directly from the electrodes and the controls on the electrodes.

The resuscitation control box can sense electrical signals from the patient's body during pauses between CPR compressions. Also, as is described below, a compression-sensing element such as an accelerometer or a force-sensing element is provided in the region of the defibrillation electrode pad on which the user presses to perform CPR. The purpose of the compression-sensing or force-sensing element is to allow the resuscitation control box to prompt the user to apply additional compression or force, or to prompt the user to cease CPR if the user is performing CPR at an inappropriate point in time.

Referring to FIG. 4, in one implementation, each electrode 12, 14 (only electrode 12 is shown) of defibrillation electrode pad 10 includes a polymer-based ink containing a silver/silver-chloride suspension, which is screen-printed on a polyester or plastic base 36. The ink is used to carry the defibrillation current. The screen-printing process first involves applying a resist layer to the polyester base 36. The resist layer is basically a loose mesh of nylon or the like, in which the holes have been filled in at some locations in the mesh. Then, the silver/silver-chloride ink is applied as a paste through the resist layer in a squeegee-like manner. The ink squeezes through the screen and becomes a solid layer. The ink may then be cured or dried. The silver/silver-chloride ink provides good conductivity and good monitoring capabilities.

Thus, the ink can be applied as pattern, as opposed to a solid sheet covering the entire polyester base. For example, U.S. Pat. No. 5,330,526 describes an electrode in which the conductive portion has a scalloped or daisy shape that increases the circumference of the conductive portion and reduces burning of the patient. A conductive adhesive gel 38 covers the exposed surface of each electrode.

In addition, electrical circuit components are also be screen printed on the base, in the same manner as flat circuit components of membrane-covered, laminated panel controls.

Referring to FIG. 3, a rigid piece 40 of hard plastic, such as PVC or polycarbonate, is laminated beneath substrate 36 and supports buttons A, B, C, and PAUSE. The rigid plastic piece 40 is glued onto substrate 36. Buttons A, B, C, and PAUSE consist of small metal dome snap-action switches that make contact between an upper conductive ink trace 42 and lower conductive ink traces 44, 46, 48, and 50. Buttons A, B, C, and PAUSE serve as controls that can be activated by the user that are physically located either on or immediately adjacent to the electrode assembly itself. Each of buttons A, B, C, and PAUSE may be associated with an adjacent light-emitting diode (LED). For example, LEDs may be glued, using conductive epoxy, onto silver/silver-chloride traces on substrate 36. An embossed polyester laminate layer 54 covers conductive ink trace 42 of buttons A, B, C, and PAUSE, and a foam layer 56 is laminated beneath rigid plastic piece 40.

Referring again to FIG. 4, defibrillation electrode pad 10 includes an extension piece that is placed directly over the location on the patient's body where the rescuer performs chest compressions. This extension piece includes substrate 36, and a semi-rigid plastic supporting member 58 laminated underneath substrate 36 that covers the chest compression area. Semi-rigid supporting member 58 provides somewhat less rigidity than rigid plastic piece 409 provided at the location of buttons A, B, C, and PAUSE (illustrated in FIG. 3).

In implementations having a force-sensing element, a polyester laminate 60, and a force-sensing resistor having two layers of carbon-plated material 62 and 64, are laminated between polyester substrate 36 and semi-rigid supporting member 58. A suitable construction of the force-sensing resistor is illustrated in the FSR Integration Guide & Evaluation Parts Catalog with Suggested Electrical Interfaces, from Interlink Electronics. The electrical contact between the two carbon-plated layers of material increases with increased pressure, and the layers of force-sensing resistive material can provide a generally linear relationship between resistance and force. Conductive ink traces 66 and 68 provide electrical connections to the two layers of the force-sensing resistor.

During chest compressions, the rescuer's hands are placed over the extension piece, and the force-sensing resistor of the extension piece is used to sense the force and the timing of the chest compressions. The force-sensing resistor provides information to the resuscitation control box so that the resuscitation control box can provide the rescuer with feedback if the rescuer is applying insufficient force. The resuscitation control box also provides coaching as to the rate at which CPR is performed. In certain situations, the resuscitation control box indicates to the rescuer that CPR should be halted because it is being performed at an inappropriate time, such as immediately prior to application of a defibrillation shock when the rescuer's hands should not be touching the patient, in which case the resuscitation control box will also indicate that the rescuer should stay clear of the patient because the patient is going to experience a defibrillation shock.

As is noted above, during CPR the rescuer pushes on the patient's chest through the extension piece in the vicinity of the electrodes. If the resuscitation control box were to perform analysis during the chest compressions, the chest compressions would be likely to affect the sensed electrical rhythm. Instead, during the pauses between sets of compressions (for example, the pause after every fifth chest compression), the resuscitation control box can perform an electrocardiogram (ECG) analysis. The resuscitation control box might discover, for example, that the patient who is undergoing CPR is experiencing a non-shockable rhythm such as bradycardia, in which case the CPR is required in order to keep the patient alive, but then the resuscitation control box may discover that the rhythm has changed to ventricular fibrillation in the midst of CPR, in which case the resuscitation control box would instruct the rescuer to stop performing CPR so as to allow the resuscitation control box to perform more analysis and possibly apply one or more shocks to the patient. Thus, the rescuer is integrated into a sophisticated scheme that allows complex combinations of therapy.

In another implementation, a compression-sensing element such as an accelerometer may be used in place of a force-sensing element. The accelerometer, such as a solid-state ADXL202 accelerometer, is positioned at the location where the rescuer performs chest compressions. In this implementation, the microprocessor obtains acceleration readings from the accelerometer at fixed time intervals such as one-millisecond intervals, and the microprocessor integrates the acceleration readings to provide a measurement of chest compression. The use of an accelerometer is based on the discovery that it is more important to measure how deeply the rescuer is compressing the chest than to measure how hard the rescuer is pressing. In fact, every victim's chest will have a different compliance, and it is important that the chest be compressed about an inch and a half to two inches in a normal sized adult regardless of the victim's chest compliance.

Figure 2:
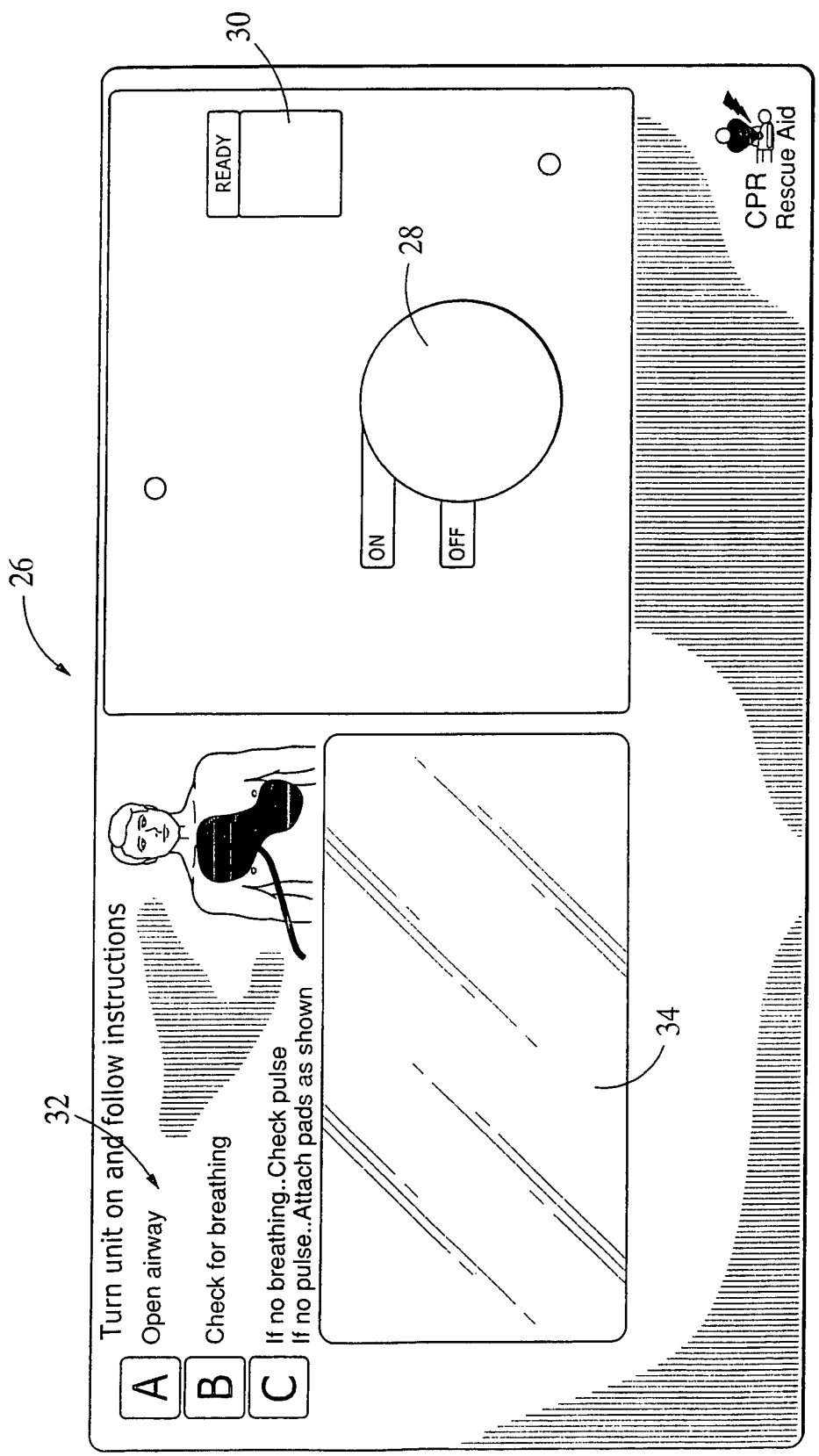
FIG. 2 is a view of the front display panel of a resuscitation control box that houses electronic circuitry and provides audible and visual prompting.
Figure 5:
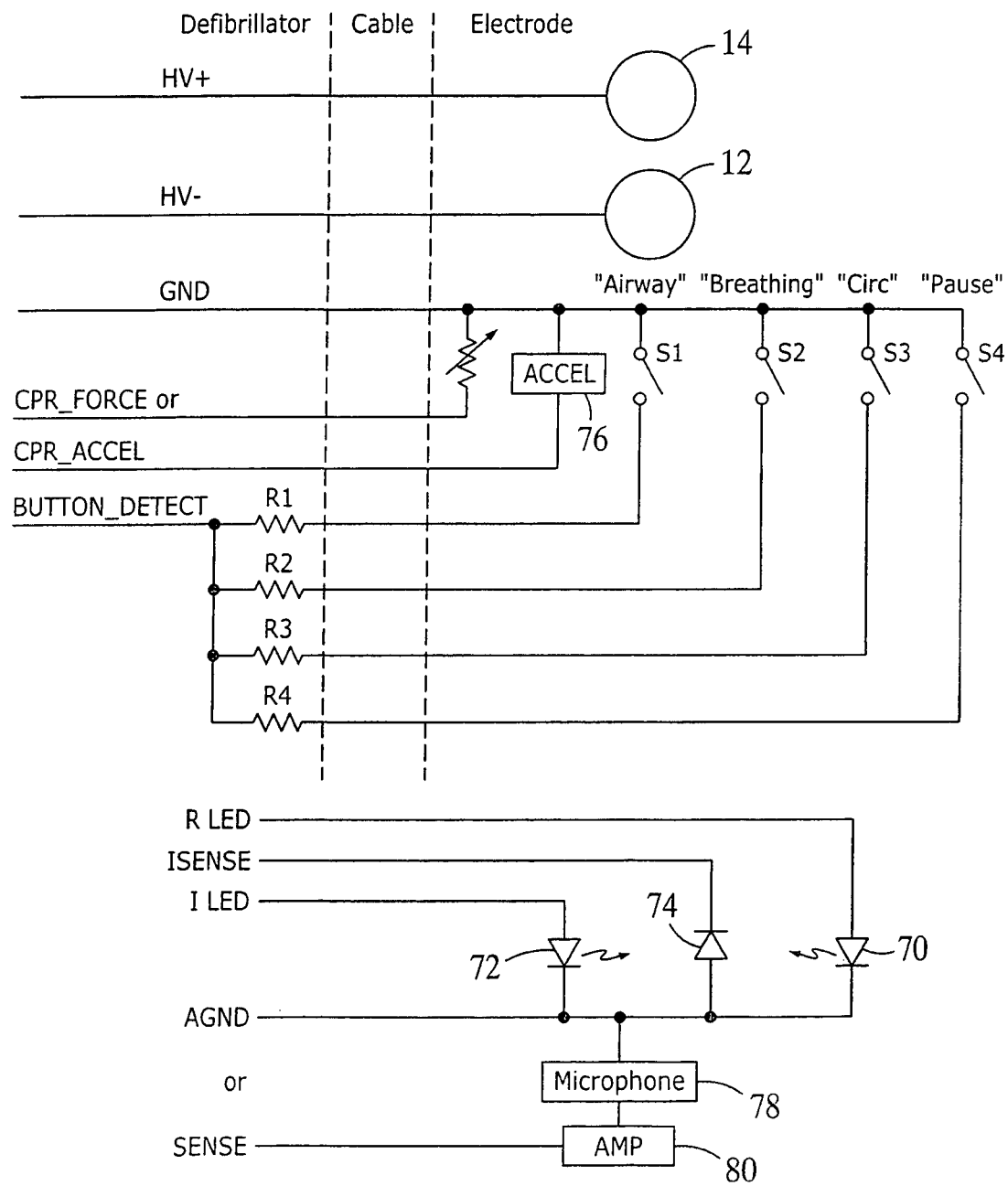
FIG. 5 is a circuit diagram illustrating the circuit interconnections between the defibrillation electrode pad of FIG. 1 and the resuscitation control box of FIG. 2.
Figure 6A:
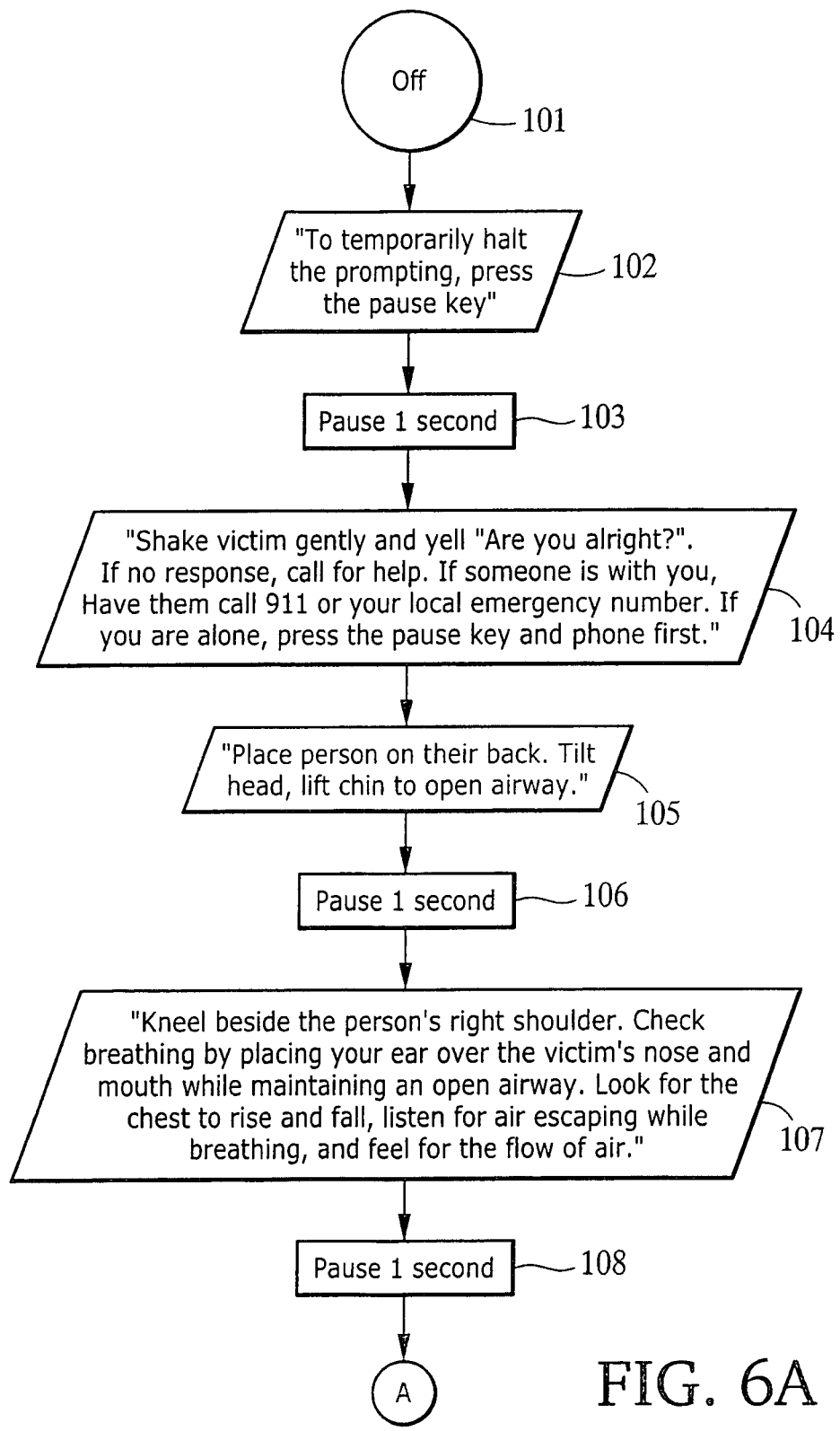
FIGS. 6A and 6B are a flowchart illustrating an initial routine of a resuscitation system.
Figure 6B:
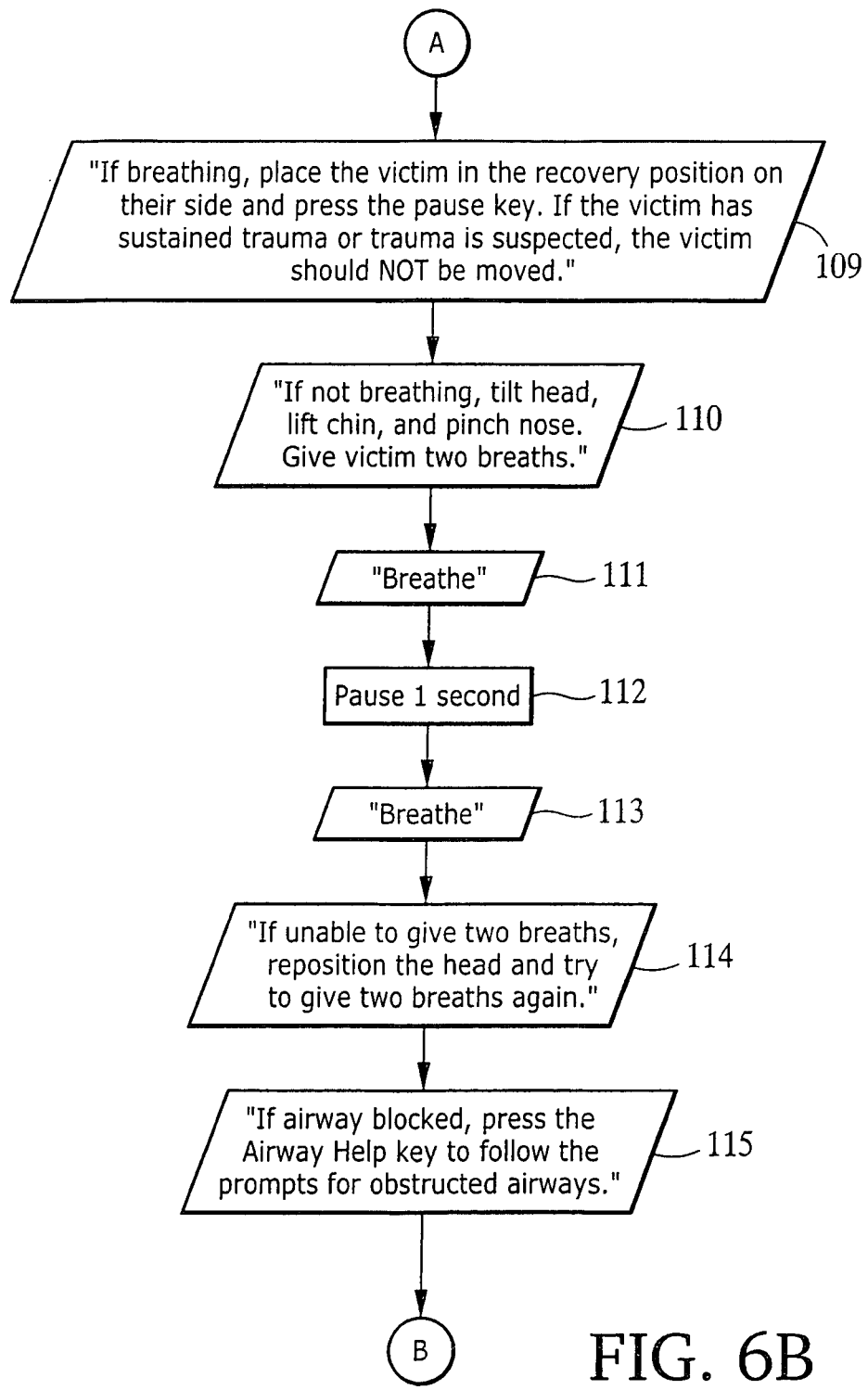
Figure 7A:
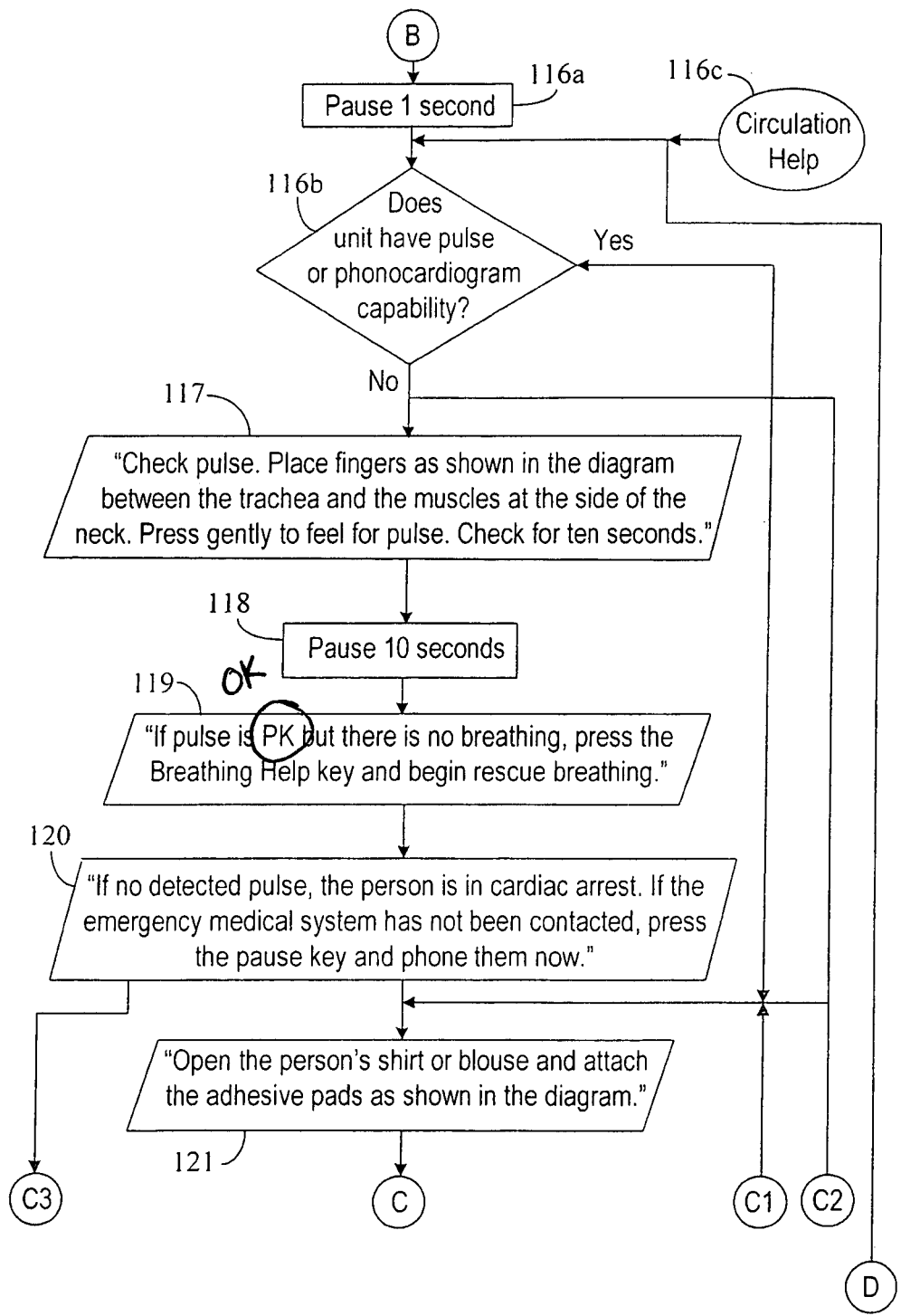
FIGS. 7A, 7B, and 7C are a flowcharts illustrating the "circulation help" routine of the resuscitation system.
Figure 7B:
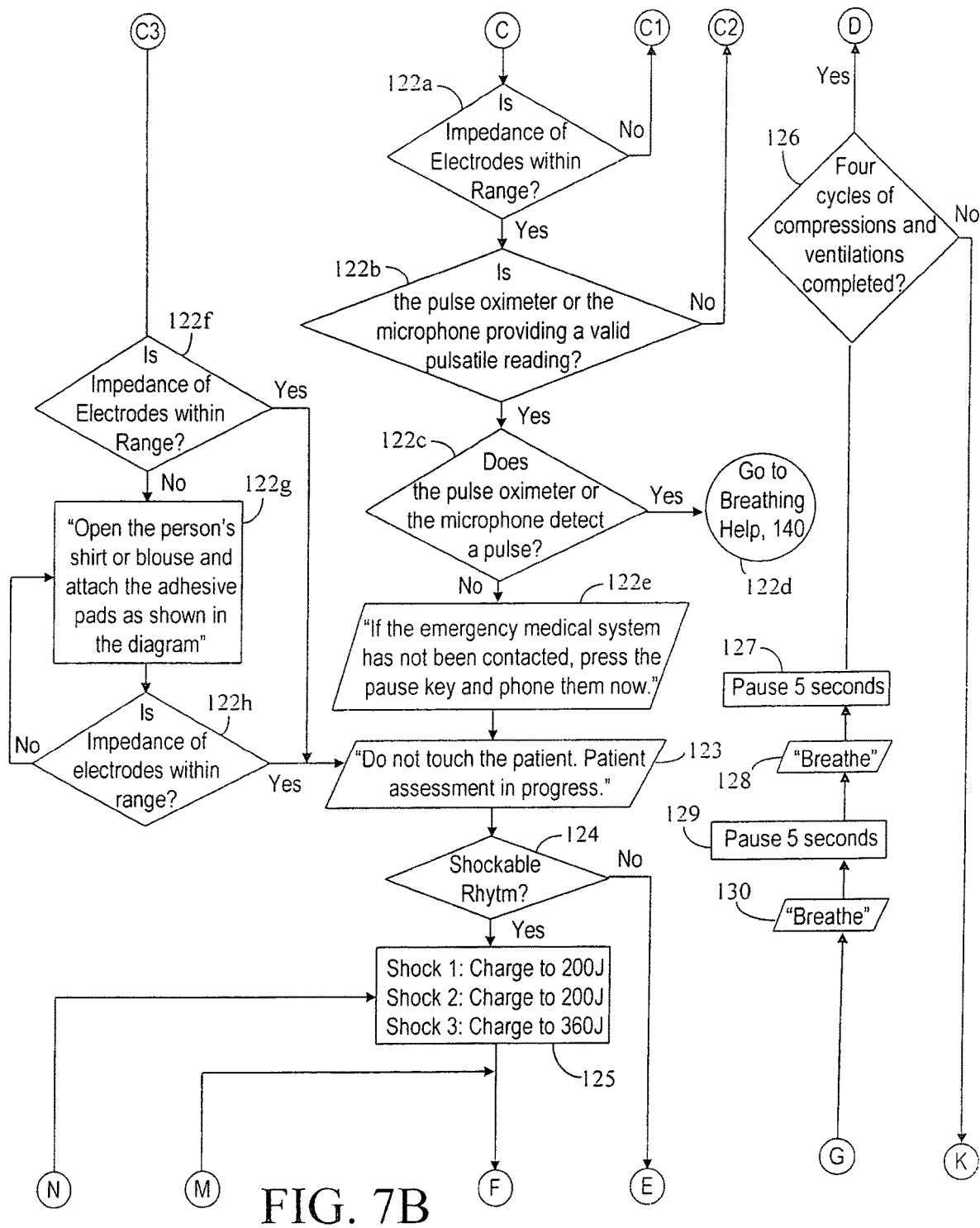
Figure 7C:
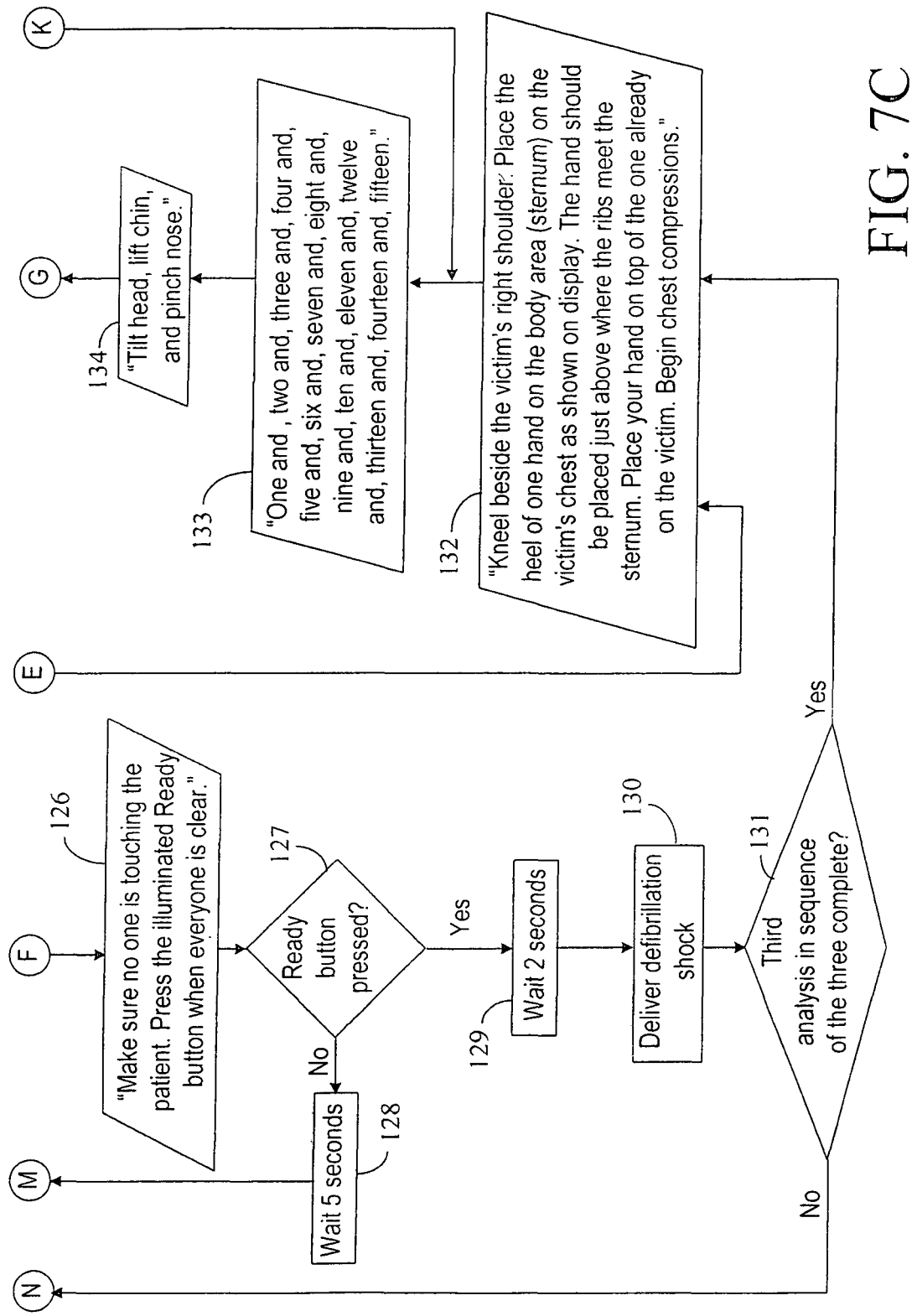

FIG. 5 is a circuit diagram illustrating the circuit interconnections between the defibrillation electrode pad of FIG. 1 through the cable to the resuscitation control box of FIG. 2. Sternum electrode 14 is connected to HV+ at the resuscitation control box, and apex electrode 12 is connected to HV−. A ground GND is connected to the upper conductive ink trace of buttons A, B, C, and PAUSE and to one of the layers of the force-sensing resistor. The other layer of the force-sensing resistor is connected to CPR_FORCE, and the lower conductive ink traces associated with buttons A, B, C, and PAUSE are connected to BUTTON_DETECT through resistors R1, R2, R3, and R4. As an alternative to the use of a force-sensing resistor, a compression-sensing accelerometer 76 may be employed, in which case CPR_FORCE is replaced by CPR_ACCEL connected to accelerometer 76. Red light-emitting diode 70, near-infrared light-emitting diode 72, and photodetector diode 74 of the pulse oximetry system are connected to RLED, ILED, and ISENSE respectively, as well as ground AGND. As an alternative to the use of a pulse oximetry system, a phonocardiogram system may be employed, in which case RLED, ILED, and ISENSE is replaced by SENSE connected to microphone 78 and amplifier 80.

FIGS. 6-9 illustrate the routine of the resuscitation system, which is based on steps A, B, and C (airway, breathing, and circulation). Because step C includes defibrillation as well as chest compressions, all of the aspects of resuscitation are tied together in one protocol (actually, if defibrillation were considered to be a step D distinct from step C, the sequence of steps would be A, B, D, C).

The first thing the rescuer must do upon arriving at the patient is to determine whether the patient is unconscious and breathing. The rescuer opens the patient's airway, administers breaths to the patient if the patient is not breathing, and checks to determine whether a pulse is present. If there is no pulse, rather than perform chest compressions as in standard CPR, the rescuer allows the resuscitation control box to analyze the patient's electrical rhythm, and if the resuscitation control box determines that the rhythm is shockable, the resuscitation control box causes one or more shocks to be applied to the patient, and then the rescuer performs chest compressions. Thus, there is provided a first response system that can keep the patient viable until an advanced life support time arrives to perform advanced techniques including pacing, further defibrillation, and drug therapy.

If the resuscitation control box determines that it should apply one or more defibrillation shocks to the patient, it is important that the rescuer not be anywhere near the patient when the shocks are applied to the patient. Prior to application of each shock, the resuscitation control box instructs the rescuer to please press the "ready" button when everybody is clear of the patient. The pressing of the "ready" button verifies that the rescuer's hands are off of the patient.

When the resuscitation control box detects a shockable rhythm, the resuscitation control box provides shocks of appropriate duration and energy (such as a sequence of shocks of increasing energy from 200 Joules to 300 Joules to the highest setting, 360 Joules, with the resuscitation control box performing analysis after each shock to determine whether another shock is required). If the defibrillation therapy is successful, the patient's rhythm is typically converted from ventricular fibrillation, ventricular tachycardia, or ventricular flutter to bradycardia, idio-ventricular rhythm, or asystole, all of which require CPR. It is rare to convert to a normal rhythm. Once the resuscitation control box has caused defibrillation shocks to be applied to the patient, the resuscitation control box automatically senses the patient's condition, and depending on the patient's condition will either prompt the responder to perform CPR or will not prompt the respond to perform CPR.

Defibrillation equipment can be somewhat intimidating to rescuers who are not medical professionals because the equipment can lead the rescuer to feel responsibility for having to save a loved one's life. It is important that the defibrillation equipment reduce this sense of responsibility. In particular, when the rescuer presses the "ready" button, rather than apply a shock immediately that will cause the patient's body to jump dramatically, the resuscitation control box will thank the rescuer and instruct the rescuer to remain clear of the patient and then wait for about two seconds (the resuscitation control box may describe this period)to the rescuer as being an internal safety check, even if no substantial safety check is being performed). This process has an effect similar to a conversation that hands responsibility to the resuscitation control box, which makes the decision whether to apply the shock. Thus, the system maintains the rescuer safety features of a semi-automatic external defibrillator, because the rescuer must press the "ready" button before each shock, while appearing to operate more as a fully automatic external defibrillator because the time delay immediately prior to each shock leaves the rescuer with the impression that operation of the equipment is out of the hands of the rescuer. The use of CPR prompts in combination with the defibrillation also adds to the sense that the rescuer is simply following instructions from the resuscitation control box.

With reference to FIGS. 6-9, when the rescuer turns the resuscitation control box on (step 101), the resuscitation control box first informs the rescuer that the rescuer can temporarily halt prompting by pressing the PAUSE button (step 102), and then, after a pause, instructs the rescuer to check responsiveness of patient, and if the patient is nonresponsive to call an emergency medical service (EMS) (steps 103, 104). The resuscitation control box then instructs the rescuer to check the patient's airway to determine whether the patient is breathing (steps 105-107).

After a pause, the resuscitation control box then instructs the rescuer that if the patient is breathing the patient should be placed on the patient's side, unless trauma is suspected, and that the rescuer should press the PAUSE button (steps 108-109). Then the resuscitation control box instructs the rescuer to perform mouth-to-mouth resuscitation if the patient is not breathing (steps 110-114). Then the resuscitation control box instructs the rescuer to press an Airway Help button A if the patient's airway is blocked, so that the resuscitation control box can give prompts for clearing obstructed airways (steps 115 of FIG. 6B and 147-158 of FIGS. 9A-9B).

Next, after a pause (step 116a), if the resuscitation control box does not include pulse oximetry or phonocardiogram capability (step 116b), the resuscitation control box instructs the rescuer to check the patient's pulse (step 117). After another pause, the resuscitation control box instructs the rescuer to press a Breathing Help button B if the patient's pulse is okay but the patient is not breathing, so that the resuscitation control box can give prompts for assisting the patient's breathing (steps 118 and 119 of FIG. 7A and 140-146 of FIG. 8). Light-emitting diodes adjacent the various buttons indicate which button has been pressed most recently (only one light remains on at a time). The resuscitation control box next prompts the rescuer to contact an emergency medical system (step 120) and to open the patient's shirt or blouse and attach the adhesive pads (steps 122f-122h).

If the resuscitation control box does include pulse oximetry or phonocardiogram capability (step and 116b), the resuscitation control box prompts the rescuer to open the patient's shirt or blouse and attach the adhesive pads (steps 121 and 122a). If the pulse oximetry or phonocardiogram system does not provide a valid pulsatile reading (step 122b), then the flow chart proceeds to step 117. If the pulse oximetry or phonocardiogram system does provide a valid pulsatile reading and detects a pulse (steps 122b and 122c), then the resuscitation control box begins the breathing help routine (steps 122d of FIG. 7B and step 140 of FIG. 8). If the pulse oximetry or phonocardiogram system does not detect a pulse, then the resuscitation control prompts the rescuer to contact an emergency medical system (step 122e), measures the impedance of the patient to determine whether it is within an acceptable range for application of shocks (step 123) and determines whether the patient's rhythm is shockable (steps 124). If the rhythm is shockable, the resuscitation control box causes a sequence of shocks to be applied to the patient, each shock requiring the rescuer first to press the "READY" button on the resuscitation control box (steps 124-131). After the last shock in the sequence, or if the rhythm is non-shockable, the resuscitation control box prompts the rescuer in CPR (steps 132-139). The flowchart then returns to step 117.

Figure 8:
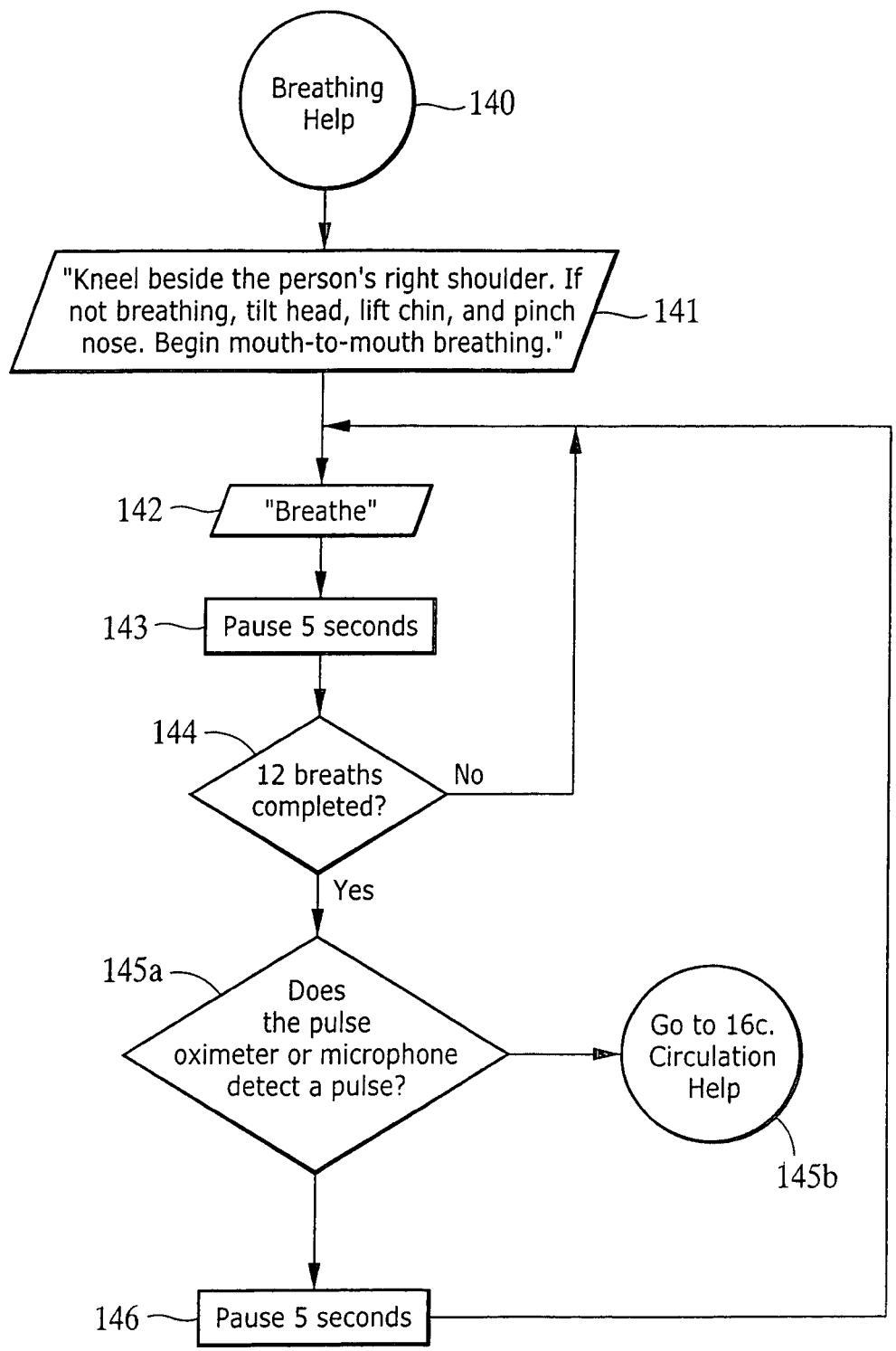
FIG. 8 is a flowchart illustrating the "breathing help" routine of the resuscitation system.
Figure 9A:
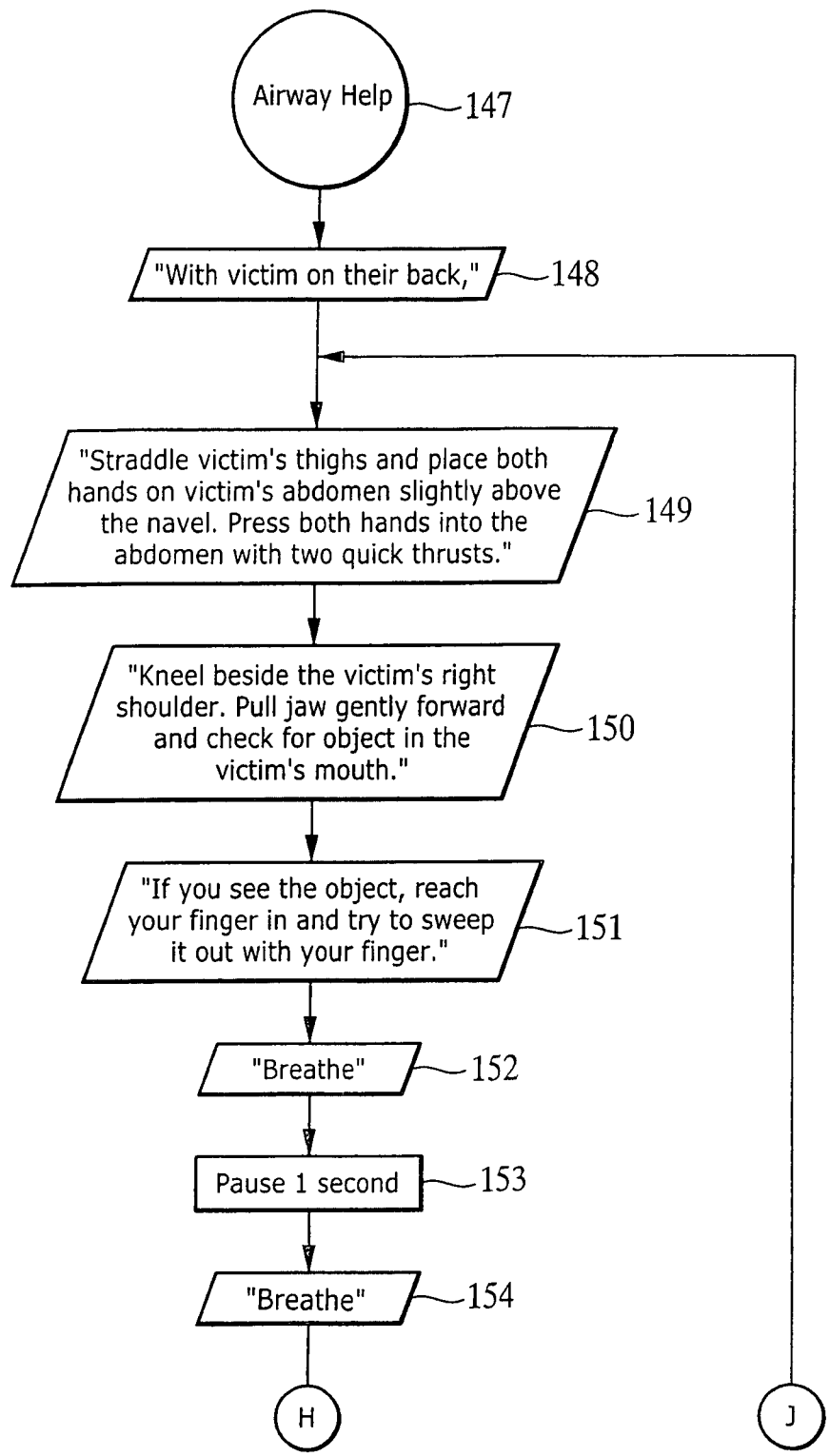
FIGS. 9A and 9B are a flowchart illustrating the "airway help" routine of the resuscitation system.
Figure 9B:
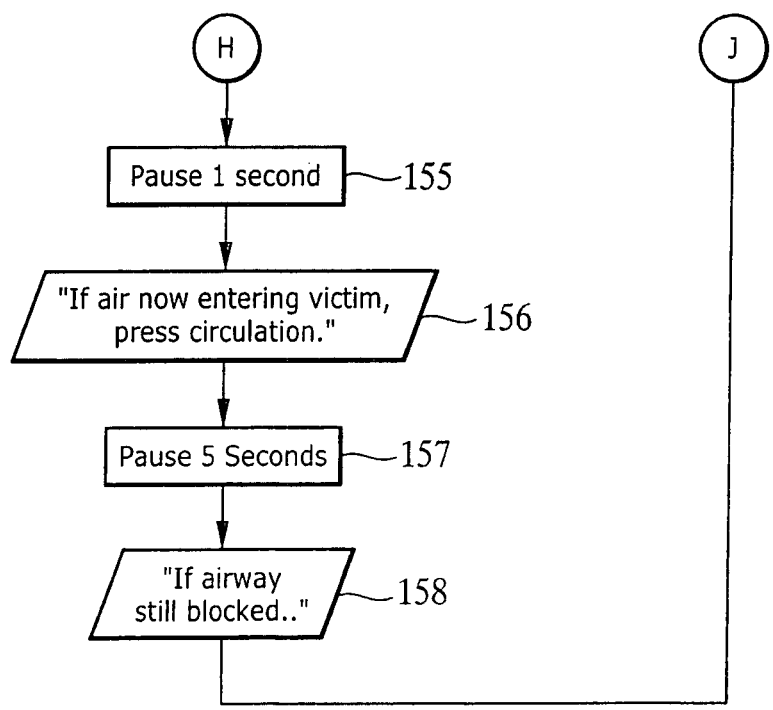
Figure 10:
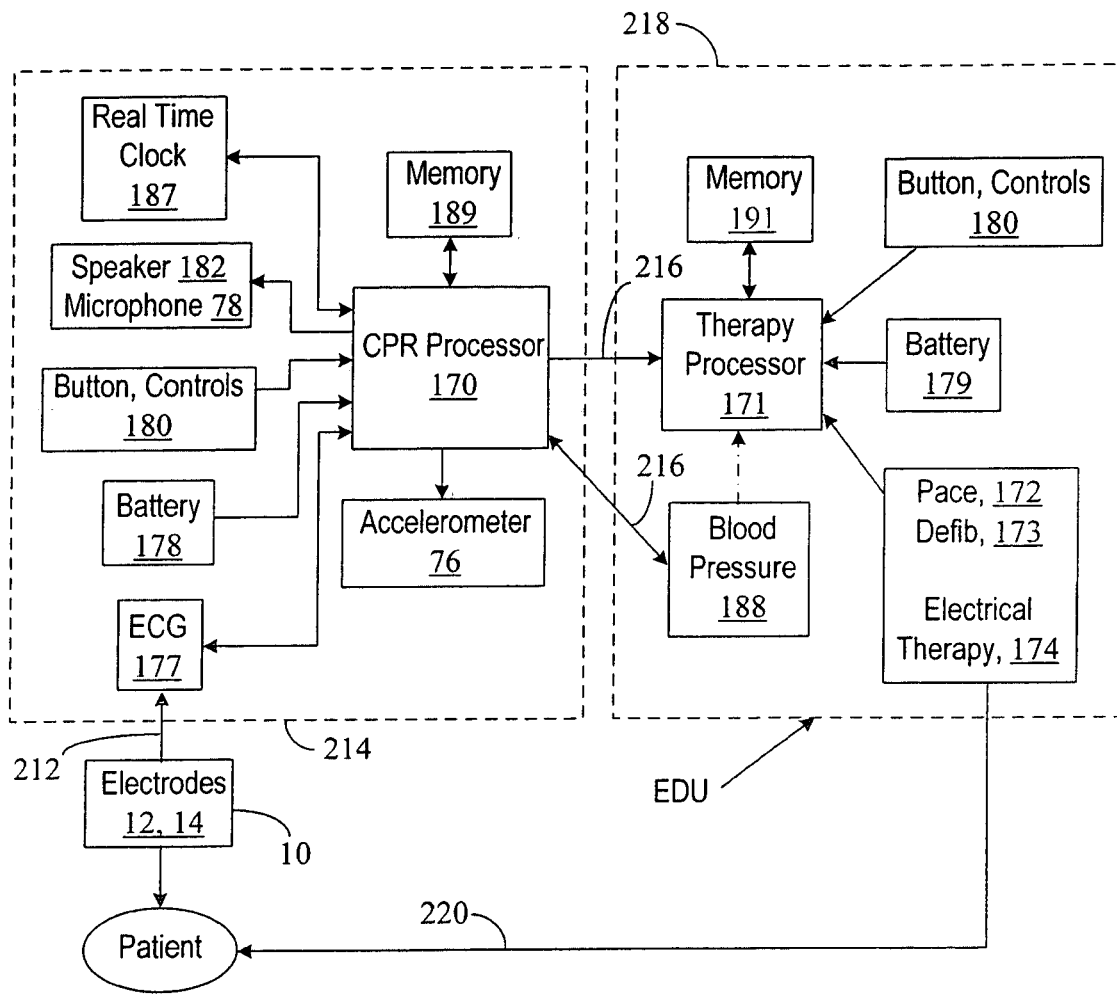
FIG. 10 is a block diagram of the electronic circuitry of a resuscitation system.
Figure 11:
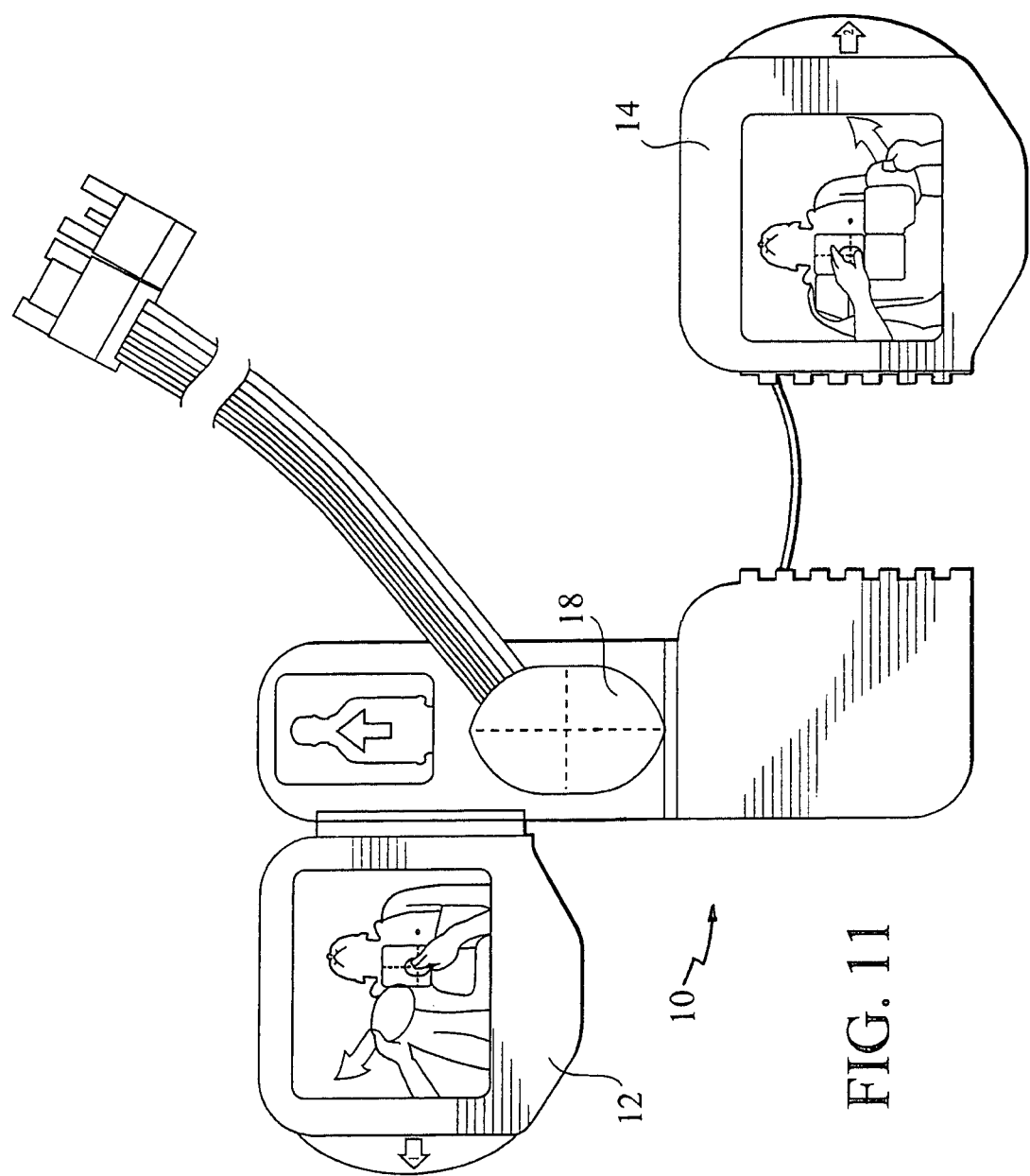
FIG. 11 is a drawing of a defibrillation electrode assembly.

FIG. 8 shows the steps 140-146 for prompting the rescuer to assist the patient's breathing. After 12 breaths have been completed (step 144), the pulse oximetry or phonocardiogram system attempts to detect a pulse (step 145a), or, if the system does not include a pulse oximetry or phonocardiogram system, the resuscitation control box prompts the rescuer to check the patient's pulse. If no pulse is present, the resuscitation control box prompts the rescuer to press a Circulation Help button C (step 145b) that brings the rescuer back to the circulation portion of the flowchart. Otherwise, if a pulse is detected, then the flow chart of FIG. 8 returns to step 142.

The combined defibrillation and CPR resuscitation assembly provided can be less intimidating than conventional AEDs because the assembly is not devoted solely to defibrillation. Moreover, the resuscitation assembly is less intimidating because it accomodates common skill retention problems with respect to necessary techniques ancillary to defibrillation such as mouth-to-mouth resuscitation and CPR, including the appropriate rates of chest compression, the proper location for performing compressions, the proper manner of tilting the patient's head. In addition, because the rescuer knows that it may never even be necessary to apply a defibrillation shock during use of the resuscitation assembly, the rescuer may be more comfortable using the resuscitation assembly for mouth-to-mouth resuscitation and CPR. Unlike previous CPR prompting devices, the rescuer would be required to place the electrode assembly on top of the patient, but the rescuer would do this with the belief that the resuscitation assembly will be sensing the patient's condition and that the likelihood that the resuscitation assembly is actually going to apply a shock is low. If, during this resuscitation process, the resuscitation control box instructs the rescuer to press the "READY" button so that a defibrillation shock can be applied, the rescuer will likely feel comfortable allowing the shock to be applied to the patient. Basically, the resuscitation assembly simply tells the rescuer what to do, and by that point, given that the rescuer is already using the assembly, the rescuer is likely simply to do what the rescuer is told to do. Essentially, the rescuer will be likely to view the resuscitation assembly as simply being a sophisticated CPR prompting device with an additional feature incorporated into it, and since rescuers are less likely to be intimidated by CPR prompting devices than AEDs, they will be likely to use the resuscitation assembly when it is needed.

Figure 12A:
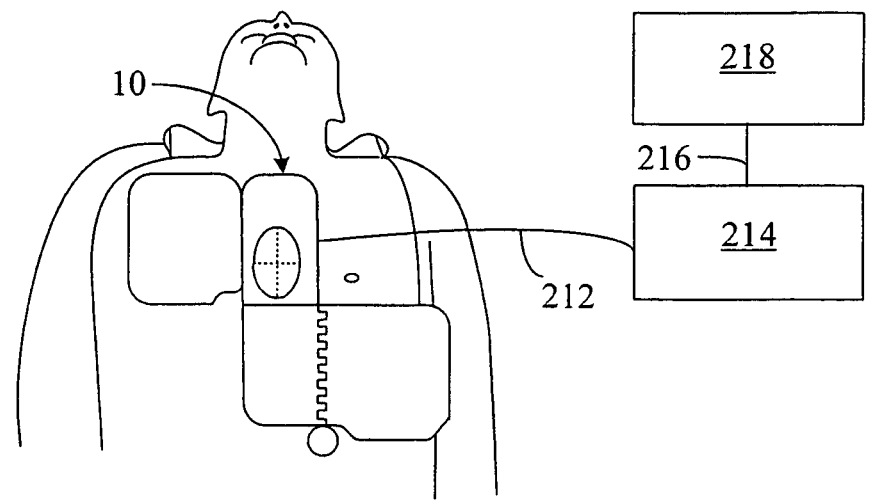
FIGS. 12A-12C are diagrammatic views of three possible implementations of first and second units.
Figure 12B:
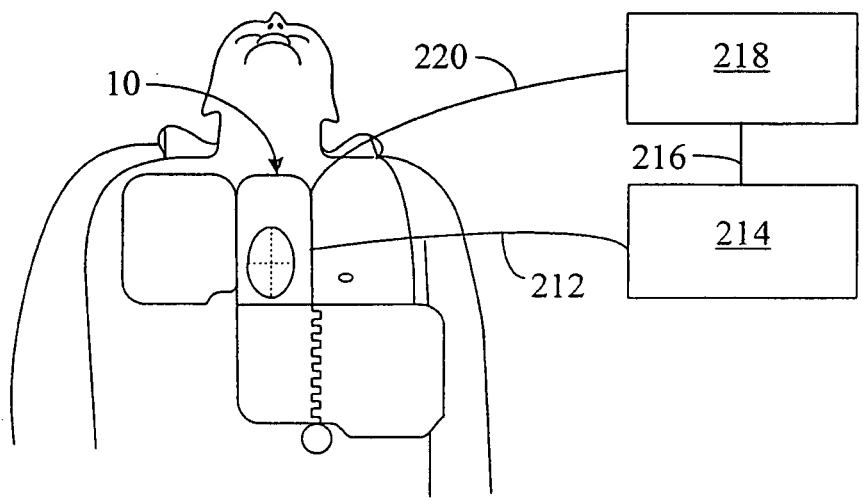
Figure 12C:
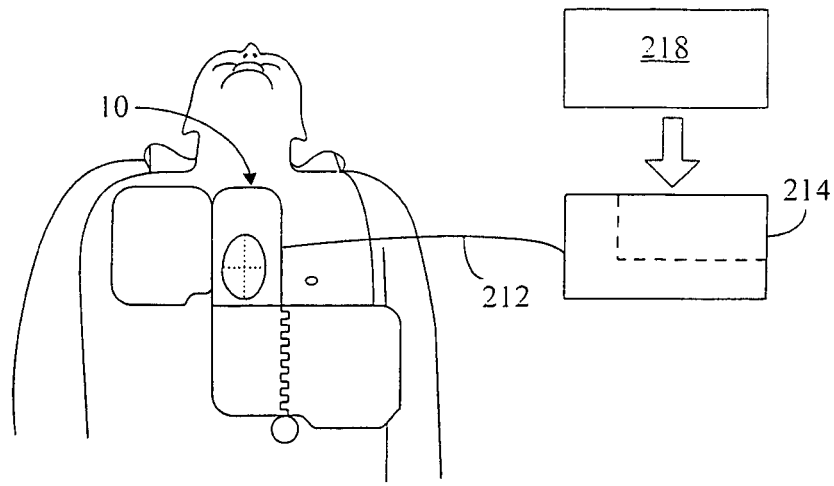

FIGS. 10, 11, and 12A-12C show alternative implementations in which an electrode pad assembly 10 is connected by a cable 212 to a first unit 214 containing the electronics for CPR prompting and resuscitation control. Another cable 216 connects the first unit to a second unit 218 containing the electronics for defibrillation and pacing therapy. A third cable 220 could be provided for making a direct connection from the second unit to the electrodes (FIG. 12B). The first unit 214 could be configured to receive the second unit 218 as an inserted module (FIG. 12C), in which case the electrical connection between the units are made internally without the use of cable 216. The primary function of the first unit 214 is to provide processing and control for CPR functions such as CPR prompts. The primary function of the second unit 218 is to provide processing and control of electrical therapy functions. The first unit includes a CPR processor 170, a battery 178, ECG circuitry 177 for amplifying and filtering the ECG signal obtained from the defibrillation pads 12, 14, a microphone 78 for recording the rescuer's voice as well as ambient sounds, an accelerometer 76, a real time clock 187, and a speaker 182 for delivering prompts to the rescuer. The second unit includes a therapy processor 171, a battery 179, buttons and controls 180, and memory 191.

The first unit could also be incorporated into the electrode pad assembly rather than being a separate box. The electronics could be provided on the rigid substrate 40 of the electrode pad assembly (FIG. 1).

Separate batteries 178, 179 and controls 180, 181 may be provided for the first (CPR) and second (therapy) units, thereby allowing the electronics in the first unit to provide CPR prompting to the operator without the need for the second unit. The cable 216 that connects the first and second units may be detachable. Memory 189 is provided in the first unit for storing information such as voice recording, ECG data, chest compression data, or electronic system status such as device failures that occur during daily self checks of the electronics initiated by a real time clock circuit.

The defibrillation electrode pad assembly 10 may incorporate defibrillation electrodes composed of a material that can be held against a patient's skin for extended periods of time (e.g., up to 30 days).

Figure 13A:
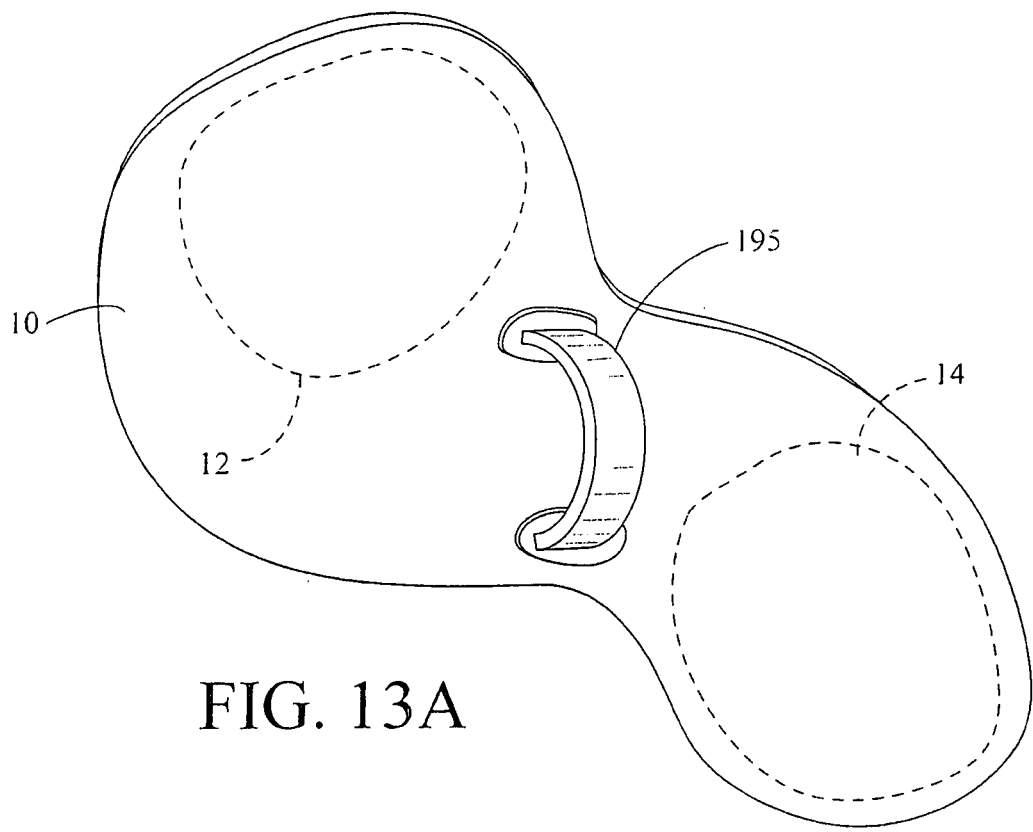
FIGS. 13A and 13B are drawings of two alternative implementations of the electrode pad assembly in which a handle is provided for the rescuer.
Figure 13B:
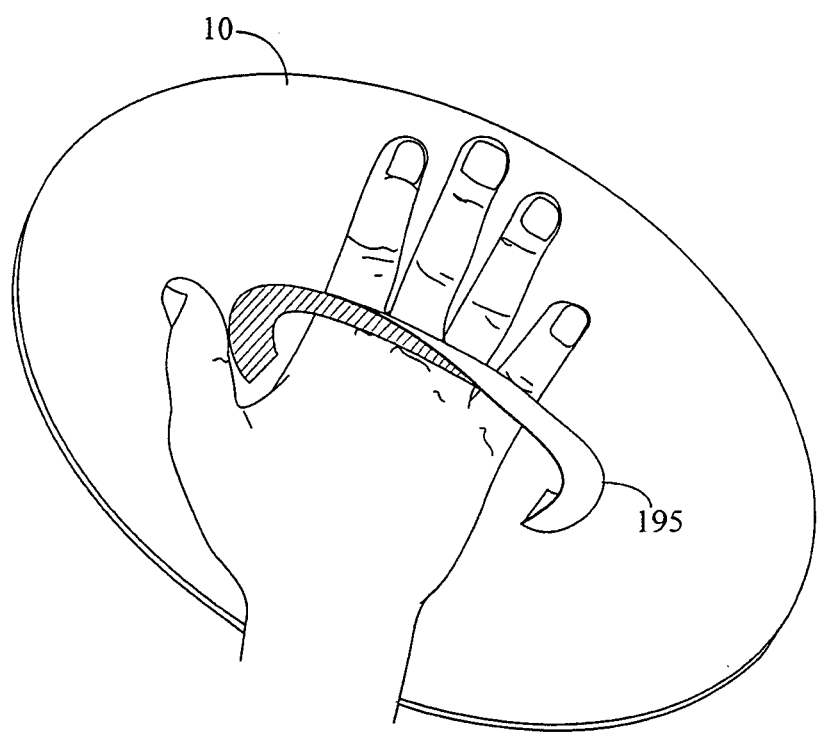

As shown in FIGS. 13A and 13B, the pad assembly 10 may also incorporate features on its upper surface facing the rescuer that provide a handle 195 for the rescuer during performance of CPR. The handle could take the form of a fabric loop (FIG. 13B) or a more rigid polymer member (FIG. 13A). The fabric could be sewn or adhered by adhesive or ultrasonic bonding to the pad 10 (FIG. 13B). The polymer handle could also be bonded by adhesive or ultrasonic bonding to the pad (FIG. 13A). It has been shown in studies that the maintenance of pressure on the chest during the decompression phase of chest compression results in a significant decrease in the effectiveness of the chest compressions. The handle 195 motivates the rescuer to pull up at least slightly during the decompression phase. The adhesive gel of the electrode pad, or other adhesive, can extend under the region where the rescuer's hands are placed during compression thus providing adhesion of the pad to the skin while the rescuer pulls on the handle during the decompression phase. Pulling up on the chest during the decompression phase has been shown to heighten negative intrathoracic pressure, increasing venous return and thus increasing blood flow during chest compressions.

In another implementation, the first unit may be adapted to be supported by the patient for long periods of time. The unit could be incorporated into the electrode pad assembly as suggested above, or it could be a separate unit configured to be worn by the patient. In such an implementation, the electronics of the first unit are designed to allow for long term monitoring of the patient's condition via the ECG 177 and physiological monitoring 176 circuitry. If a physiological condition is detected that is deemed hazardous to the patient by the CPR processor 170, based on analysis of the ECG and other physiological parameters, an alarm is sounded to the patient via the speaker 182.

An activity sensor and associated circuitry can inform the CPR processor of whether the patient is moving. For example, accelerometer 76 could serve as the activity sensor, and detect whether or not the patient is moving. Patient motion may be detected using a variety of different algorithms, including, for example the following: The acceleration signal is integrated over one-second intervals to provide an estimate of velocity. Velocity is integrated over the same one-second intervals to provide an estimate of displacement. The root means square velocity is calculated for each one-second interval. If either the RMS velocity exceeds 0.2 cm/s or the peak displacement exceeds 0.5 cm, the patient is determined to be moving.

If the algorithm determines that a cardiac emergency event is occurring, the first unit can send a message directly to a medical emergency response system, such as 911. This can be done using a variety of known communication techniques, e.g., Bluetooth, cellular phone, Ultra Wideband (UWB). If the activity sensor has determined that the patient is still moving during the cardiac emergency, the unit could also issue a prompt indicating, "Call 911 Immediately!"

The first unit will be able to determine the orientation of the patient, e.g., based on the accelerometer output. It can detect if a patient has fallen down and initiate a message to the emergency system. It can also determine whether the patient is lying on his back, the proper orientation for doing CPR. Thus, a specific prompt can be provided to the rescuer that tells them to roll the patient on their back prior to beginning CPR, should the device detect an improper orientation of the patient.

Other implementations may include signal analysis software for predicting the risk of a heart attack. When a threshold is exceeded in the value of that risk probability, a voice prompt may be provided to the patient via the speaker 182 to contact the medical emergency system. By using the motion detection capabilities of the accelerometer to measure and track a patient's activity level (PAL), and combining the activity level calculation with measurements of the ECG 177, e.g., ST-segment elevation (STE), the first unit is able to provide a predictor of the risk of an impending heart attack or cardiac arrest. An ST segment elevation exceeding a threshold such as 300 microvolts on the ECG provides an indicator of impending heart attack. In the preferred embodiment, ST segment elevation in the presence of increased physical activity is an indication of further risk of potential cardiac arrest. The calculation of risk probability may be accomplished by first performing a logistic regression of variables such as STE and PAL as predictors of cardiac arrest within 24 hours. The calculation may take the form of a linear regression equation such as $$0.24 STE + 0.12 PAL = \text{RISK}.$$

Alternatively, nonlinear regression may be performed to allow for a multiplicative term such as $$0.24 STE + 0.12 PAL + 0.54 (STE*PAL) = \text{RISK}.$$

The multiplicative term heightens the importance of STE in the presence of PAL.

Parameters such as STE, PAL and RISK may additionally be stored in memory and multiple readings and calculations performed over time. The sequence of readings may then be analyzed for trends in the physiological state of the patient that can augment the RISK calculation taken at a single point in time. For instance, if STE is found to be steadily rising over a series of readings, the voice prompt may be triggered sooner than at a fixed threshold of 300 microvolts.

Additionally, the ECG may be analyzed to determine the interval between adjacent R-waves of the QRS complexes and using this interval to calculate heart rate variability as a running difference between adjacent R-R intervals. It is known that the R-R interval will vary following an ectopic beat or ventricular premature contraction (VPC). In a healthy heart, the R-R interval will decrease immediately following the VPC followed by a gradual return to steady state; a heart with an increased risk of heart attack will show a decreased level of variability. This effect is sometimes called heart rate turbulence. Two variables are calculated: (1) the Relative Change in R-R interval (RCRR) between pre- and post-VPB R-R intervals, $$RCRR = (R\text{-}R \text{ pre-}VPB - R\text{-}R\text{post-}VPB)/R\text{-}R \text{ pre-}VPB$$

and (2) the slope of the change of R-R interval (SRR) while it is undergoing its post-VPB decrease. If the RCRR is non-negative and the slope SRR does not steeper than −2 ms/ R-R interval then the patient is considered as at risk. Alternatively, the individual calculations may be included along with STE and PAL to create an integrated measurement vector as discussed in the preceding paragraphs. Other signal analysis algorithms may incorporate analysis of heart rate variability in the frequency domain, wavelet domain or using non-linear dynamics-based methods.

Since VPBs are often rare events, the defibrillation electrode pad 10 may include circuitry to stimulate the patient with a single pulse of low enough amplitude to cause a VPB without undue discomfort to the patient, under the patient's control. An additional control is provided on the low-profile button panel 20 so that the patient may initiate the pulse under their control. Alternatively, the device is programmed to automatically deliver the pulse at regular intervals such as at 24-hour intervals, at a time of day when the patient may conveniently have access to the device, such as in the morning. While the pulse generator 186 may be located in the second (therapy) unit, it is preferably contained as part of the first (CPR) unit.

In another implementation, the activity monitoring capability of the first unit may be utilized so that the activity state of the patient is continuously monitored. Using the activity monitoring capability and a real time clock 187, the first unit may detect when a patient has woken up in the morning. After there has been 10 minutes of regular motion detected, the unit may prompt the patient that it would like to perform a test. If the patient assents to the test indicated by a press of the TEST button on the low-profile button panel 20, the unit will send out a small current pulse, preferably a 40 millisecond pulse of 75 mA amplitude that is synchronized to the patient's ECG so that it occurs approximately 200 mS prior to the R-wave and after the T-wave so as not to introduce any arrhythmias. The pulse will safely cause a VPB in the patient which can then be used to measure the autonomic response to a VPB to provide regular calculations of the autonomic response to a VPB as measured by such parameters, though not limited to, STE and PAL, and providing a daily update to the RISK calculation.

Additional physiological measurement, preferably that of blood pressure, may be incorporated into the RISK calculation. A sudden change in systolic or mean arterial blood pressure of greater than 10-15 points is indicative of an increased risk of cardiac arrest. In the preferred embodiment, the blood pressure measurement device would be a handheld, inflated cuff blood pressure device 188. The blood pressure cuff 188 would have wireless communication capability with the CPR Processor 170 and at the conclusion of each measurement, the blood pressure reading along with a date and time stamp would be stored in memory 189 of the CPR Processor 170 for subsequent use in calculating RISK. This scheme would allow the patient to carry the small blood pressure cuff along with them during their daily activities and take blood pressure measurements at regular intervals without having to return home. Alternatively, the blood pressure measurement device may communicate with the therapy processor and may additionally get power from and be physically connected to the second (therapy) unit by a cable. The patient will then be required to take regular blood pressure readings at the second unit, typically a larger device that may or may not be portable. Communication of the blood pressure readings may be accomplished over a cable between the first (CPR) and second units (therapy) units, e.g., cable 216, or wirelessly, using such technology as Bluetooth.

The second unit 218 may in some implementations be thought of as an energy delivery unit (EDU), in which case it would incorporate a defibrillator 172, pacer 173, or other electrical therapy 174. In some implementations, the EDU would be small and light enough to be worn in a harness or belt to be carried around continuously by the patient. The EDU 218 may in some cases not contain a therapy processor 171, but be a "dumb" device that requires the controls provided by connection to the processor in the first (CPR) unit, e.g., on the defibrillator pad 10, in order to deliver electrical therapy to the patient.

In some cases, the patient may not even own an EDU due to the significant costs inherent in the high-voltage components necessary. The patient would only own the first unit and defibrillator pad, as the components incorporated in them are less expensive, e.g., they can be manufactured from less-expensive, consumer-type electronics. In such a case, when the patient did not own the EDU, and had a heart attack, a bystander or family member who encountered the cardiac arrest victim would be prompted to begin CPR. It has been shown now in several studies that performing good CPR for extended periods prior to delivery of a shock are not only not detrimental to long term survival, but in fact increase survival rates. CPR would thus begin with built-in prompting and when the paramedic arrives with the defibrillator it can be connected to the pads to deliver the electrical therapy. If the first (CPR) unit is separate from the electrode pad assembly, the EDU connection to the electrodes could be direct, or via a cable connected to the first (CPR) unit. If the defibrillator is an EDU or other compatible device, patient and performance data stored by the first (CPR) unit may be downloaded to the defibrillator.

The defibrillation pads 10, 12 may be separable from the CPR-prompting first unit and be connected at the time that the EDU is brought to the scene; the defibrillation pads may be connected both electrically and mechanically to the CPR-prompting first unit at that time. A greater amount of the control functionality may be put into the first unit, leaving essentially only the circuitry for providing the defibrillation pulses in the second unit. The first unit may be incorporated into the defibrillation electrode pad assembly, or made a separate unit connected to the pad assembly by one or more cables. The second unit may connect to the first unit by one or more cables, or by a wireless connection. The defibrillation pulses may pass through the first unit (FIG. 12A), or be routed directly to the defibrillation electrodes via one or more cables running from the second unit to the electrodes (FIG. 12B). The second unit may connect to the first unit by being plugged into the first unit (FIG. 12C), without the need for a cable (e.g., the second unit could be a defibrillation module that plugs into the first unit).

In some implementations the second (therapy) unit can provide pacing therapy as well as defibrillation therapy. Pulse detection methods other than pulse oximetry and phonocardiogram may be employed. Any method capable of detecting a victim's pulse can be used for pulse detection.

Figure 14:
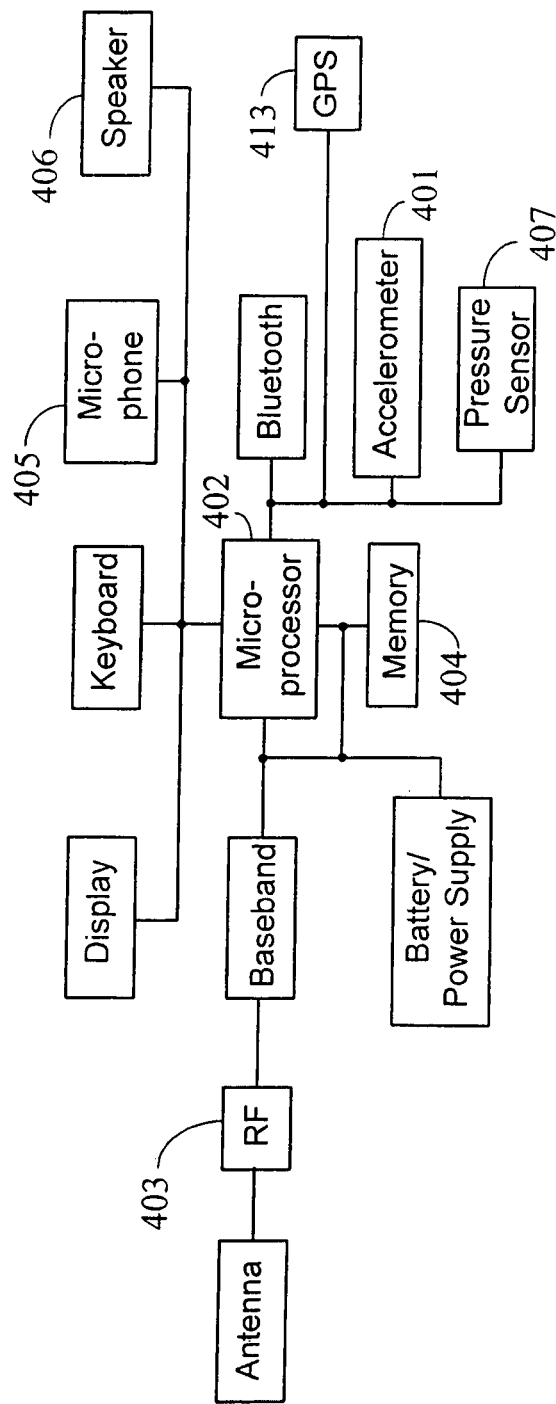
FIG. 14 is a block diagram of the electronic circuitry of an implementation including a cell phone.
Figure 15A:
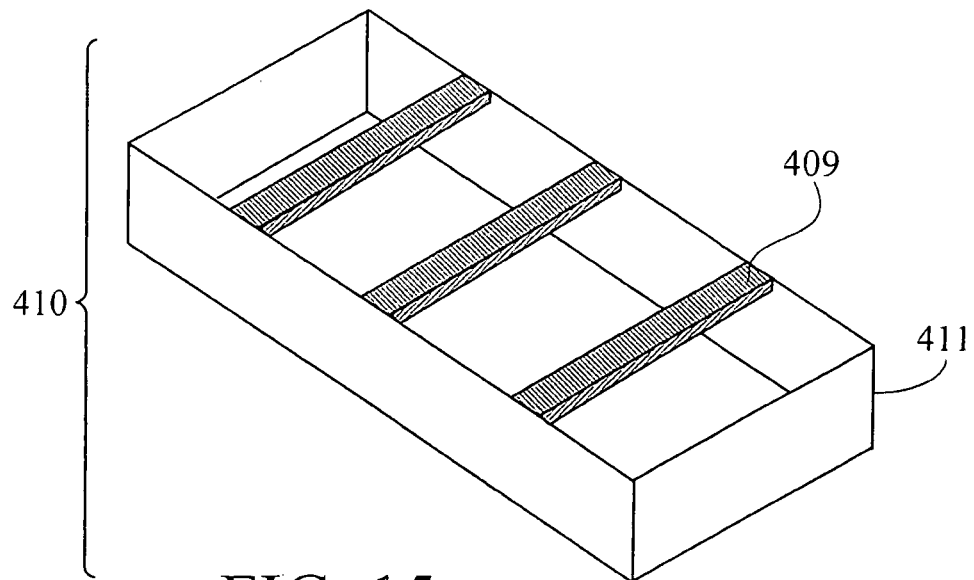
FIGS. 15A-15B are perspective views of the exterior of the implementation of FIG. 14.
Figure 15B:
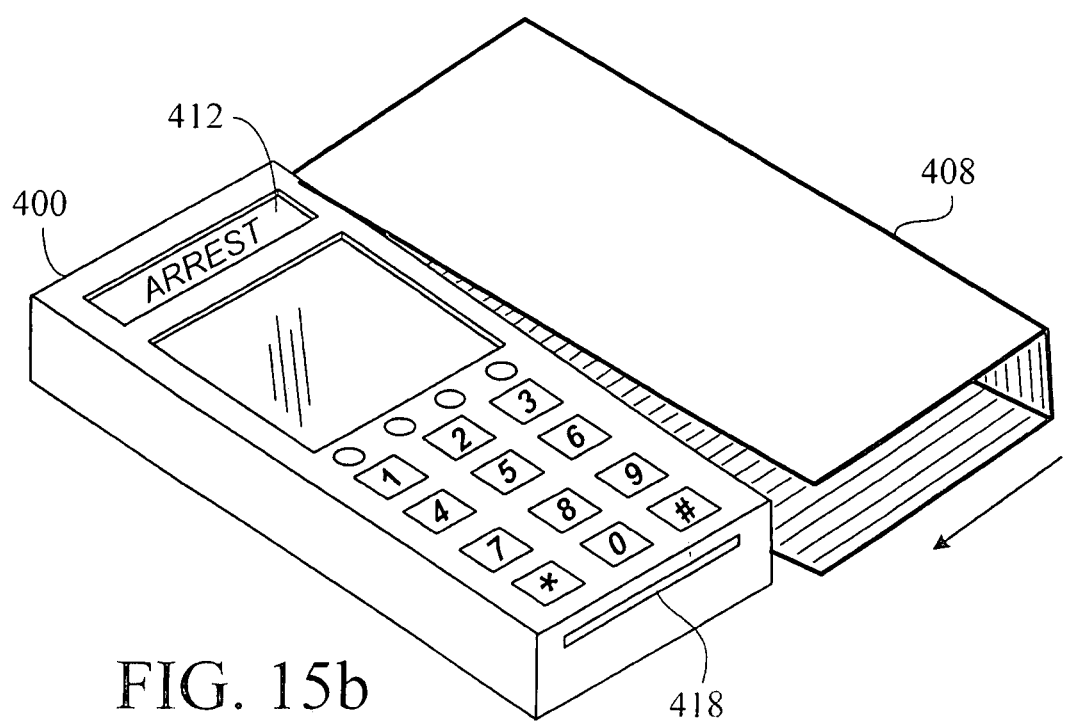
Figure 16:
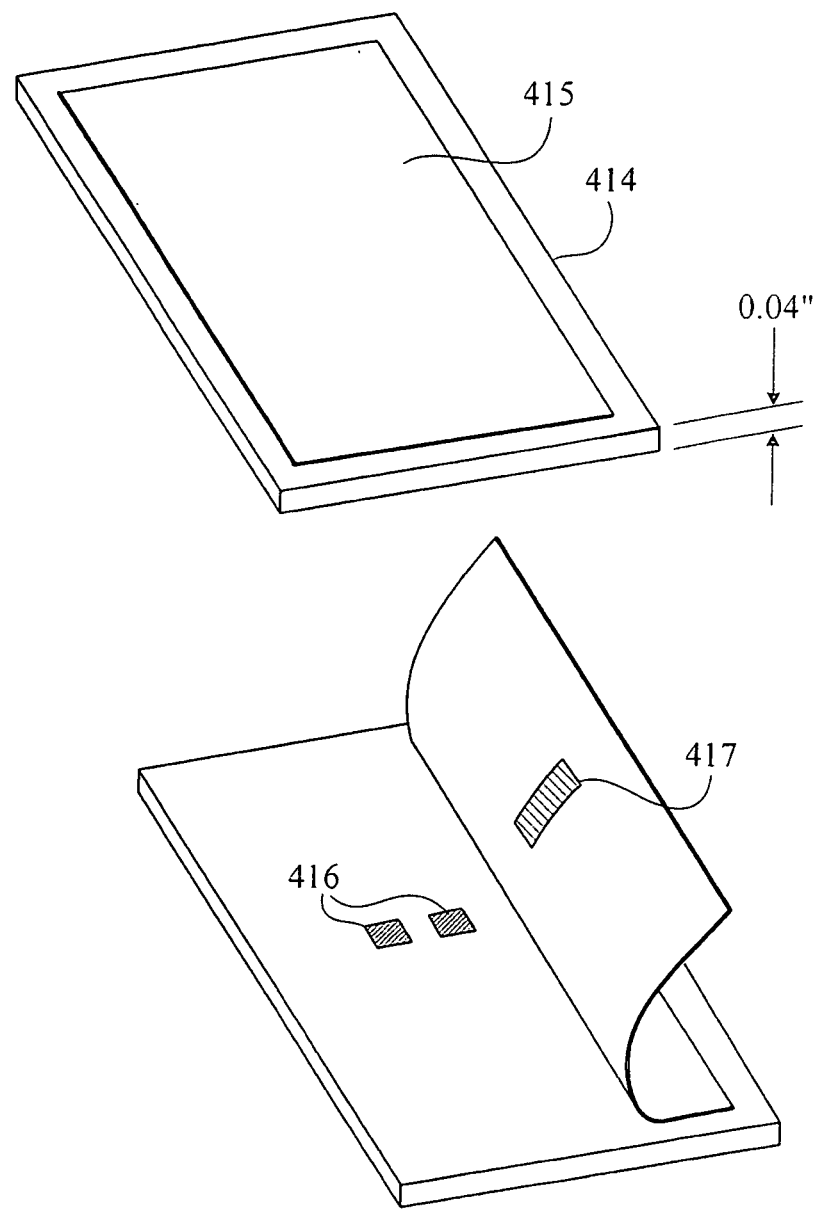
FIG. 16 is a perspective view of a further implementation.

FIGS. 14-16 describe other implementations, including implementations in which the CPR-prompting first unit is configured for connection to a defibrillation unit, as well as implementations in which the first unit is not configured for connection to a defibrillation unit. In the latter case, the defibrillation unit may be used without being connected to the CPR-prompting unit.

Referring to FIG. 14, the CPR-prompting unit may be a cell phone or other handheld computing/communication device such as a personal digital assistant (PDA) or a wireless e-mail handset (e.g., a Blackberry). The handheld computing/communication device may incorporate a motion detection element (e.g., a MEMS-based semiconductor inertial sensing system such as that manufactured by Analog Devices, of Massachusetts) along with the processing, data storage, and speaker elements. The handheld device may also incorporate RF communications circuitry and a microphone, as would be the case if the device is a cell phone. The motion detection element may comprise an accelerometer and or a pressure-sensing element (e.g., a piezoelectric strain gauge or pressure-sensitive resistor)

In the case of the device being a cell phone, the same DSP processing unit used to handle speech and baseband signal processing may be used to process the output of the accelerometer or pressure sensor, e.g., to derive a displacement measurement of chest compressions.

In some implementations, the cell phone 400, itself, is placed on the patient's sternum during CPR, and the rescuer's hands are placed on top of the phone to apply force to the patient's chest. Structural elements may be incorporated into or adjacent the cell phone 400 to allow the rescuer to exert the force necessary for an effective chest compression. The structural elements may take the form of an external storage case for the phone, or they may be internal elements 410 within the phone, e.g., struts 409 and rigid sidewalls 411 (FIG. 15A), or the phone may be supported within a rigid clamshell 408 slid over the phone (FIG. 15B).

A dedicated cardiac arrest key 412 may be provided on the cell phone, or CPR prompting functions may be activated by using the phone's standard scrolling and menu functionality. Activation of CPR prompting, may also initiate a call to emergency medical services, e.g., "911". On activation of the emergency and connection to 911, a speakerphone may be engaged on the cell phone, to facilitate communication between the rescuer and emergency services.

Light emitting diodes and sensors 70, 72, 74 or ECG electrodes 12, 14 may be incorporated into the surface of the phone so that when the phone is placed on the patient's sternum, the presence or absence of a pulse may be detected. The ECG system may incorporate a transthoracic impedance measurement method such as by using a small high frequency signal (preferably 2 microamps in amplitude and 60-100 kilohertz in frequency) By synchronously demodulating the signal and measuring both current and voltage, an impedance measurement can be made. Utilizing the impedance measurement, the breathing rate and duty cycle can be determined.

As resuscitation progresses, the rescuer may interact with the 911 operator to gain additional confidence and encouragement. The cell phone may include geolocator technology such as GPS (global positioning system).

The CPR prompting and feedback function of the cell phone (or other handheld computing/communication device) may also be used in conjunction with a separate CPR-assistance element worn or applied to the patient. The CPR-assistance element communicates (e.g., wirelessly) with the cell phone. The CPR-assistance element may be applied to the patient at the time of cardiac arrest or earlier (it could also be worn continuously by the patient). The element may be a watch (e.g., as manufactured by Polar Heart Rate Monitors, of New York) or a flat element incorporated into a self-adhesive strip adhered (e.g., vertically) along a patient's sternum.

FIG. 16 shows one possible implementation of such a CPR-assistance element—a thin card 414, approximately the thickness of a credit card (0.04 inches), which houses an accelerometer, processor and necessary memory, battery, and wireless communication (e.g., Bluetooth for communication with the cell phone). On one side of the card is a self-adhesive label 415 that when removed turns the device on (e.g., via a set of contacts 416 on the card and a shorting strip 417 located on the facing surface of the self-adhesive release liner). When the self-adhesive surface is exposed, the card is affixed to the patient's sternum, and serves as the location at which chest compression forces are applied to the patient.

CPR-assistance element 414 may incorporate a wireless communication capability (e.g., Bluetooth) that, when a cardiac arrest or impending cardiac arrest is detected or predicted, communicates with the cell phone and begins a protocol for CPR. Because the bulky element of the CPR prompting unit (e.g., the speaker, power hungry DSP signal processor, RF communication circuitry, and larger battery) are incorporated into the cell phone (or other handheld computing/communication device), the CPR-assistance element applied to the patient's chest (with, e.g., an accelerometer or pressure sensor, and an ECG sensor) can be much thinner. This allows for the possibility of the CPR feedback function being small enough to be stored in a wallet.

The handheld computing/communication device may communicate with a separate defibrillation unit (or the CPR-assistance element may communicate with the defibrillation unit). ECG analysis may be performed in the defibrillation unit, in the handheld device, or in the CPR-assistance element. The defibrillation unit may be controlled by the handheld device.

Figure 17:
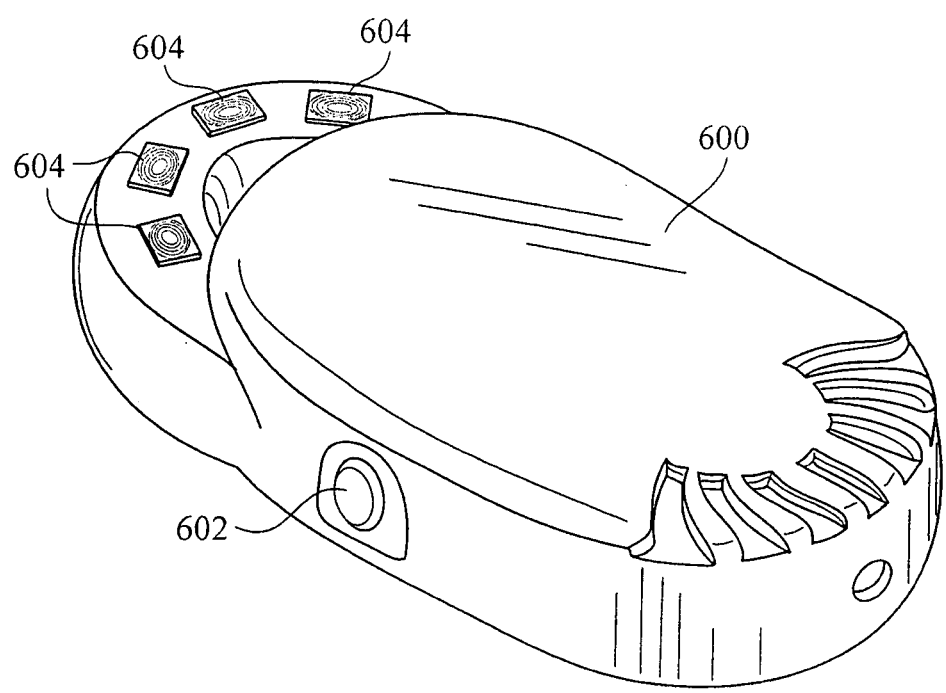
FIG. 17 is a perspective view of a further implementation.

FIG. 17 shows another implementation in which at least some of the functions of the CPR-assistance element and at least some of the resuscitation functions of the handheld computing/communication device are combined in one handheld resuscitation device 600. The device is battery powered, and can be used for both CPR training and as a CPR coaching device during rescues. Circuit elements similar to those described in connection with the implementations of FIGS. 14-16 would be provided in the device, including a microprocessor, memory, speaker, visual display elements, and accelerometer. The device provides spoken reminders of proper CPR technique and real time feedback on the rate and depth of chest compressions. An on/off switch 602 is pressed to activate the device. Initially, the device delivers a series of prompts reminding the user of the appropriate resuscitation steps. These include:

Stay Calm
    Check Responsiveness
    Call for Help
    Check Airway
    Check Breathing
    Begin CPR The device then produces a series of beeping sounds at a rate of 100 per minute to assist the user in timing chest compressions. When chest compressions are detected by an accelerometer built into the device, the device performs integration operations on the output of the accelerometer to estimate the depth of chest compressions. After ten seconds of compressions, the device delivers one of the following messages:

Good Compressions
    Push Harder

An algorithm in the processing performed by the device sets a standard for the number of good compressions (e.g., a minimum of 3.75 cm of chest displacement) as a percentage of the number of total compressions. If the percentage exceeds the minimum for good CPR, the message "Good Compressions" will be played. Otherwise, "Push Harder: will be played. After twenty seconds, the message "Give Breaths" will be played. The device then returns to the same state that followed the message "Start CPR". Each time the beeper sounds, a number of lights 604 will be turned on to indicate the depth of the last compression. E.g., if the last compression was a good compression, all four lights could be turned on. If not, only one light might be turned on (or anywhere from one to three lights could be turned on to show the degree by which the compression failed to qualify as a good compression).

Various other features can be included in device 600. Switch 602 could also be used to switch modes; e.g., if the switch button is depressed more than two seconds, a voice prompt would allow selection of adult mode, pediatric mode, training mode or some other mode. Labels could be placed on the device (e.g., indicating how to use the device, and the need to call for help. A disposable sticky adhesive pad could be provided to enable placement on the patient. A GPS circuit could provide location of rescue and aid in locating the device. A mechanical dome switch could be included on the top or bottom surface to provide the user with tactile feedback of proper release of the chest (e.g., hearing a snapping sound would indicate release). The device could be configured to determine whether chest release was correct, and prompt the user accordingly. Different types of indications could be used to prompt user as to whether a compression was good or bad. Wireless communication (e.g., Bluetooth) could allow communication with external devices (the device could be configured to communicate with a cell phone or other handheld computing/communication device, e.g., as does the device of FIG. 16). ECG could be sensed through an electrode on surface of device (as described in connection with the implementation of FIG. 16), and ECG processing could provide a prompt to "Call for AED". A graphic display (e.g., LCD) could provide information on compression depth, ECG analysis, heart rate, compression rate, breath timing. The compression rate beeping reminder tone could be user disabled. Data recording capability could be included, for later playback. A microphone could be added to record voice and environmental sounds during a rescue. A connector could be provided for making a wired connection to an AED or other device. Processing could determine that compressions exceeded a safe displacement (e.g., greater than 2 inches), and an appropriate warning prompt issued. The visual indication of compression depth could be maintained for a short period (e.g., 10 seconds) after compression stops to enable a user to observe their performance during a break from compressions. A headphone jack could be provided for the user to hear prompts over a headphone. Additional processing and different chest compression prompts could be provided, e.g., "too slow", "too fast", "too shallow", "too deep", and "incomplete release".

Many other implementations of the invention other than those described above are within the invention, which is defined by the following claims. For example, although mention has been made of particular protocols for cardiac arrest or other conditions, the invention is not limited to the mentioned protocols. A ventilation sensor could provide information on ventilation to assist in resuscitation (e.g., providing signals to the cell phone). The ventilation sensor could be a sensor configured to make measurements of transthoracic impedance, breathing sounds, or airway pressure (e.g., a pressure sensor connected by tubing to a breathing tube or adapter, as described in the commonly owned U.S. application Ser. No. 11/384,218, filed on Mar. 17, 2006, entitled "Automated Resuscitation Device with Ventilation Sensing and Prompting," and issued as U.S. Pat. No. 7,747,319. Various other types of handheld computing/communication devices could be used instead of the specific examples given, so long as the device is of a handheld size and is configured to perform some type of non-resuscitation function involving computing or communication.

What is claimed is:

1. A handheld cell phone configured to be held by the hands of a rescuer while the hands of the rescuer provide cardiopulmonary resuscitation (CPR) chest compressions for a patient, the handheld cell phone comprising:
    a housing;
    a motion sensor disposed within the housing;
    a cell phone display screen provided on the housing and configured to provide a menu comprising a CPR prompting option; and
    a processor, a memory, and associated circuitry disposed within the housing and communicatively coupled with the motion sensor and the cell phone display screen, the processor being configured to:
        receive the motion sensor signal from the motion sensor indicative of the CPR chest compressions, and
        process the motion sensor signal to derive CPR performance data,
    wherein a user selection of the CPR prompting option at the menu provided on the cell phone display screen
        (a) initiates a communication to emergency medical services (EMS),
        (b) activates the processing of the motion sensor signal to derive the CPR performance data, and
        (c) activates real-time CPR prompts comprising:
            one or more of a prompt to begin CPR, a prompt to stay calm, a prompt to check responsiveness, a prompt to call for help, a prompt to check airway, and a prompt to check breathing, and
            at least one prompt based on the derived CPR performance data according to a user selected CPR prompting mode,
    wherein the processor is configured to receive the motion sensor signal, derive the CPR performance data, and control the cell phone display screen without defibrillation capability.

2. The handheld cell phone of claim 1 comprising structural elements configured to enable the handheld cell phone to be held by the hands of the rescuer during the CPR chest compressions and withstand a chest compression force exerted by the rescuer during the CPR chest compressions.

3. The handheld cell phone of claim 2 wherein the structural elements comprise one or more of an external storage case, struts, rigid sidewalls, and an external rigid clamshell.

4. The handheld cell phone of claim 1 comprising circuit elements configured to provide a spatial location.

5. The handheld cell phone of claim 1 wherein the motion sensor comprises an accelerometer configured to sense acceleration of the chest of the patient.

6. The handheld cell phone of claim 1 comprising an audio output device, wherein the processor is further configured to control the audio output device to provide at least one of verbal instructions and audio prompts for the rescuer.

7. The handheld cell phone of claim 1 wherein the real-time CPR prompts comprise CPR compression depth prompts and CPR compression rate prompts.

8. The handheld cell phone of claim 1 wherein the processor is configured to activate a speakerphone capability of the handheld cell phone in response to the initiation of the communication to emergency medical services.

9. The handheld cell phone of claim 1 wherein the handheld cell phone is configured to establish a wireless communicative coupling with a defibrillation device.

10. The handheld cell phone of claim 9, wherein the handheld cell phone is configured to provide the CPR performance data to the defibrillation device via the wireless communicative coupling with the defibrillation device.

11. The handheld cell phone of claim 9, wherein the wireless communicative coupling is a short-range wireless connection.

12. The system of claim 1, wherein the at least one prompt based on the derived CPR performance data according to the user selected CPR prompting mode comprises at least one of a "good compressions" message and a "push harder" message.

13. The handheld cell phone of claim 1 comprising at least one sensor configured to detect a pulse of the patient and wherein the cell phone display screen is configured to provide a heart rate of the patient based on the detected pulse.

14. The handheld cell phone of claim 13, wherein the at least one sensor is configured to detect the pulse of the patient when the handheld cell phone is placed on a patient's sternum.

15. The handheld cell phone of claim 1, wherein the initiated communication to EMS includes a request for a defibrillation device.

16. The handheld cell phone of claim 1, wherein the processor is configured to prompt a selection of the user selected CPR prompting mode from available options comprising an adult mode and a pediatric mode.

17. The handheld cell phone of claim 1, wherein the processor is configured to switch to a CPR training mode based on a user input.

18. The handheld cell phone of claim 1, wherein the processor is communicatively coupled with a ventilation sensor and configured to receive ventilation signals from the ventilation sensor.

19. A system for assisting a rescuer in resuscitating a patient, the system comprising:
   a defibrillation device; and
   a handheld cell phone configured to establish a wireless communicative coupling with the defibrillation device, the handheld cell phone comprising:
     a housing,
     a motion sensor disposed within the housing,
     a cell phone display screen provided on the housing and configured to provide a menu comprising a CPR prompting option, and
     a processor, a memory, and associated circuitry disposed within the housing and communicatively coupled with the motion sensor and the cell phone display screen,
   wherein the processor is configured to:
     receive the motion sensor signal from the motion sensor indicative of cardiopulmonary resuscitation (CPR) chest compressions, and
     process the motion sensor signal to derive CPR performance data,
   wherein a user selection of the CPR prompting option at the menu provided on the cell phone display screen
     (a) initiate a communication to emergency medical services (EMS),
     (b) activates the processing of the motion sensor signal to derive the CPR performance data, and
     (c) activates real-time CPR prompts comprising:
       one or more of a prompt to begin CPR, a prompt to stay calm, a prompt to check responsiveness, a prompt to call for help, a prompt to check airway, and a prompt to check breathing, and
       at least one prompt according to a user selected CPR prompting mode and based on the derived CPR performance data,
   wherein the processor is configured to receive the motion sensor signal, derive the CPR performance data, and control the cell phone display screen without defibrillation capability,
   wherein the handheld cell phone is configured to be held by the hands of the rescuer while the hands of the rescuer provide the CPR chest compressions for the patient, and
   wherein the defibrillation device is configured to receive the CPR performance data from the handheld cell phone via the wireless communicative coupling.

20. The system of claim 19 wherein the handheld cell phone comprises structural elements configured to enable the handheld cell phone to be held by the hands of the rescuer on the sternum of the patient during the CPR chest compressions and withstand a chest compression force exerted by the rescuer during the CPR chest compressions.

21. The system of claim 20 wherein the structural elements comprise one or more of an external storage case, struts, rigid sidewalls, and an external rigid clamshell.

22. The system of claim 19 wherein the handheld cell phone comprises circuit elements configured to provide a spatial location.

23. The system of claim 19 wherein the motion sensor comprises an accelerometer configured to sense acceleration of the chest of the patient.

24. The system of claim 19 wherein the handheld cell phone comprises an audio output device and wherein the processor is further configured to control the audio output device to provide at least one of verbal instructions and audio prompts for the rescuer.

25. The system of claim 19 wherein the real-time CPR prompts comprise CPR compression depth prompts and CPR compression rate prompts.

26. The system of claim 19 wherein the wireless communicative coupling with the defibrillation device is a short-range wireless connection.

27. The system of claim 19 wherein the processor of the handheld cell phone is configured to activate a speakerphone capability of the handheld cell phone in response to the initiation of the communication to emergency medical services.

28. The system of claim 19, wherein the at least one prompt according to the user selected CPR prompting mode and based on the derived CPR performance data comprises at least one of a "good compressions" message and a "push harder" message.

29. The system of claim 19, wherein the handheld cell phone comprises at least one sensor configured to detect a pulse of the patient and wherein the cell phone display screen is configured to provide a heart rate of the patient based on the detected pulse.

30. The system of claim 29, wherein the at least one sensor is configured to detect the pulse of the patient when the handheld cell phone is placed on a patient's sternum.

31. The system of claim 29, wherein the handheld cell phone is configured to provide the heart rate based on the pulse detection to the defibrillation device via the wireless communicative coupling with the defibrillation device.

32. The system of claim 19, wherein the processor is configured to prompt a selection of the user selected CPR prompting mode from available options comprising an adult mode and a pediatric mode.

33. The system of claim 19, wherein the processor is configured to switch to a CPR training mode based on a user input.

34. The system of claim 19, wherein the processor is communicatively coupled with a ventilation sensor and configured to receive ventilation signals from the ventilation sensor.

* * * * *